(12) United States Patent
Ho

(10) Patent No.: US 11,849,778 B2
(45) Date of Patent: Dec. 26, 2023

(54) GARMENT STRUCTURE HAVING ADJUSTMENT MECHANISM FOR ABUTTING AT LEAST ONE PAD UNIT FIRMLY AGAINST SKIN TO PROVIDE AT LEAST ONE OF ELECTROTHERAPY AND HEAT THERAPY

(71) Applicant: Hoi Ming Michael Ho, Tuen Mun (HK)

(72) Inventor: Hoi Ming Michael Ho, Tuen Mun (HK)

( * ) Notice: Subject to any disclaimer, the term of this patent is extended or adjusted under 35 U.S.C. 154(b) by 538 days.

(21) Appl. No.: 16/926,643

(22) Filed: Jul. 10, 2020

(65) Prior Publication Data

US 2022/0007750 A1   Jan. 13, 2022

(51) Int. Cl.
*A41D 1/00*     (2018.01)
*A61N 1/36*     (2006.01)
(Continued)

(52) U.S. Cl.
CPC ......... *A41D 13/0051* (2013.01); *A41D 1/002* (2013.01); *A61F 7/007* (2013.01);
(Continued)

(58) Field of Classification Search
CPC ...... A61F 2007/0018; A61F 2007/0022; A61F 2007/0023; A61F 2007/0024; A61F 2007/0026; A61F 2007/0027; A61F 2007/003; A61F 7/007; A61F 2007/0071; A61F 2007/0088; A61F 7/02; A61F 2007/0225; A61F 2007/0228; A61F 2007/023; A61F 2007/0233; A61F 2007/0234; A41D 1/002; A41D 13/0051;
(Continued)

(56) References Cited

U.S. PATENT DOCUMENTS 5,601,618 A    2/1997  James
7,072,721 B1 * 7/2006  Trent ................... A61B 5/6831
                                                    600/382
(Continued)

FOREIGN PATENT DOCUMENTS

CN      2857512 Y     1/2007
DE   202005005374 U1  6/2005
(Continued)

*Primary Examiner* — Kaitlyn E Smith
*Assistant Examiner* — Bradford C. Blaise
(74) *Attorney, Agent, or Firm* — CIPO IP Group

(57) ABSTRACT

A garment structure having an adjustment mechanism for abutting at least one pad unit against a human body includes a garment body, at least one adjustment belt, and at least one pad unit being an electrode pad unit, a heating pad unit, or an electrode pad unit with a heating unit. The adjustment belt has one end connected to the garment body, and another end fixed to an outer surface of the garment body. When the adjustment belt is pulled tight, the garment body is dragged to move toward the skin. The pad unit is disposed on the garment body, and moves, along with a portion of the garment body being dragged, to abut against the skin. A user wearing the garment structure can pull and secure the adjustment belt to enable the pad unit to easily and quickly abut against the skin to proceed with electrotherapy and/or heat therapy.

28 Claims, 18 Drawing Sheets

(51) Int. Cl.
*A61N 1/04* (2006.01)
*H05B 3/34* (2006.01)
*A61F 7/00* (2006.01)
*A61F 7/02* (2006.01)
*A41D 13/005* (2006.01)

(52) U.S. Cl.
CPC ....... *A61N 1/0408* (2013.01); *A61N 1/36021* (2013.01); *H05B 3/342* (2013.01); *A61F 2007/003* (2013.01); *A61F 2007/0023* (2013.01); *A61F 2007/0078* (2013.01); *A61F 2007/023* (2013.01); *A61F 2007/0228* (2013.01); *A61F 2007/0231* (2013.01); *A61F 2007/0233* (2013.01); *A61F 2007/0234* (2013.01); *A61N 1/0484* (2013.01)

(58) Field of Classification Search
CPC ................ A61N 1/0408; A61N 1/0484; A61N 1/36014; A61N 1/36021; H05B 3/342
See application file for complete search history.

(56) References Cited

U.S. PATENT DOCUMENTS

| | | | |
|---|---|---|---|
| 2002/0058972 A1* | 5/2002 | Minogue | A61N 1/321 607/72 |
| 2002/0077688 A1 | 6/2002 | Kirkland | |
| 2002/0107543 A1* | 8/2002 | Voznesensky | A61F 7/007 607/3 |
| 2009/0227857 A1* | 9/2009 | Rowe | A61B 5/25 600/392 |
| 2010/0257655 A1 | 10/2010 | Nilforushan et al. | |
| 2012/0144551 A1* | 6/2012 | Guldalian | A61N 1/0484 2/102 |
| 2013/0085317 A1 | 4/2013 | Feinstein | |
| 2013/0204169 A1 | 8/2013 | Poepperling et al. | |
| 2013/0345778 A1 | 12/2013 | Woods | |
| 2015/0083705 A1 | 3/2015 | Cronn et al. | |
| 2015/0374045 A1* | 12/2015 | Codner | A61F 7/02 2/455 |
| 2016/0331959 A1* | 11/2016 | Hsieh | A61F 7/02 |
| 2017/0340226 A1* | 11/2017 | Takagahara | A61B 5/28 |
| 2018/0098879 A1* | 4/2018 | Smith | F25D 3/08 |
| 2019/0298987 A1* | 10/2019 | Freeman | A61N 1/3904 |
| 2020/0155345 A1* | 5/2020 | Gaimon | A61F 13/0273 |
| 2021/0037900 A1* | 2/2021 | Itao | A61F 7/007 |
| 2021/0251802 A1* | 8/2021 | Dijkstra | A41D 1/002 |
| 2021/0259911 A1* | 8/2021 | Earsley | A61F 7/007 |

FOREIGN PATENT DOCUMENTS

| | | |
|---|---|---|
| DE | 202008003043 U1 | 5/2008 |
| DE | 202009015379 U1 | 3/2010 |
| DE | 202016107036 U1 | 3/2018 |
| EP | 1829580 A1 | 9/2007 |
| JP | S60-141846 U | 9/1985 |
| JP | H03-075754 U | 7/1991 |
| JP | H17-2005095200 A | 4/2005 |
| JP | H18-3123032 U | 7/2006 |
| JP | H21-2009533196 A | 9/2009 |
| JP | H24-2012050702 A | 3/2012 |
| JP | H26-2014235783 A | 12/2014 |
| JP | H30-2018000838 A | 1/2018 |
| JP | H30-2018183480 A | 11/2018 |
| JP | R01-2019150544 A | 9/2019 |
| WO | 02074109 A2 | 9/2002 |

\* cited by examiner

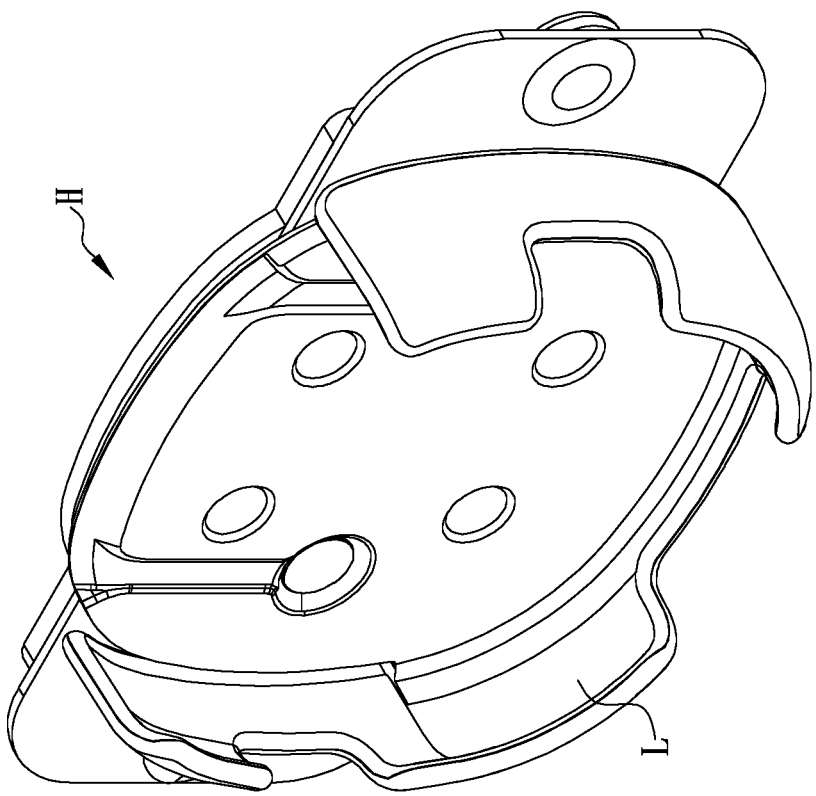
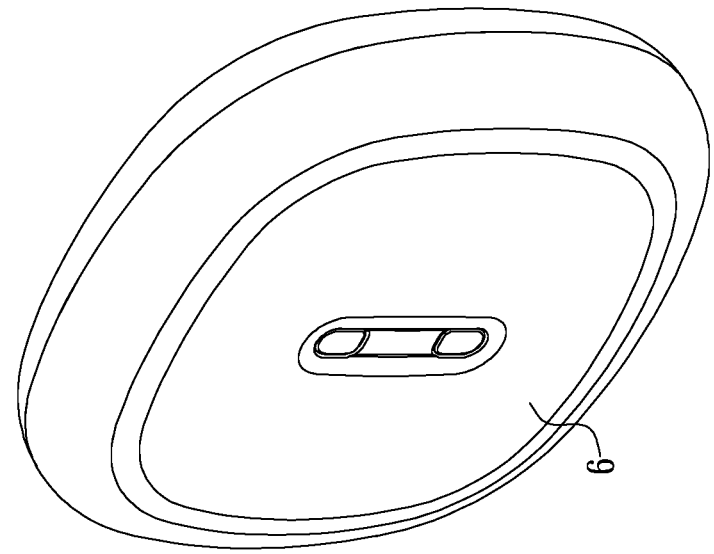
FIG. 15

GARMENT STRUCTURE HAVING ADJUSTMENT MECHANISM FOR ABUTTING AT LEAST ONE PAD UNIT FIRMLY AGAINST SKIN TO PROVIDE AT LEAST ONE OF ELECTROTHERAPY AND HEAT THERAPY

FIELD

The present disclosure relates to a garment structure, and more particularly to a garment structure that has at least one adjustment belt attached onto the garment.

BACKGROUND

Work, exercise, injuries, stress and aging can all cause muscle tension and pain. The most common area of pain for an adult is in the lower back, neck and shoulders. A majority of adults experience pain sometime in their life time. Minor muscle ache been untreated over time can become chronic disabling pain. Repetitive strain on muscles resulting from manual labor, sports, using electronic devices, driving, sleeping in a wrong way, prolonged sitting in bad posture or repetitive motions can all cause muscle tension and pain. Many people wake up with back pain, neck pain and/or tension in their shoulders. When they go to work, their muscle tension and pain often gets worse by the jobs they have to do. Consequently, after returning home from work, the aggravated pain routinely deprives them of good quality sleep at night. This routine can lead to a vicious cycle of pain growing. Worse yet, most people do not have the time or money for regular clinical treatments. Therefore, their minor pain becomes recurrent, severe chronic pain. Many athletes, office workers, manual workers doing intense labor, drivers, students, or service workers working on their feet can suffer from back pain, neck pain and/or tension in their shoulders every day. People with pain, stress or injuries, and whose daily work or other activities put their body through physical strain, should ideally have regular treatments to help relax their strained muscles, improve local circulation and relieve their pain on a daily basis, so as to stop the vicious cycle of pain growing and to prevent chronic pain. The treatments need to be easily self-administered, be available anytime, be portable so can be used at work, at home and during travel, and be effective and easy to be incorporated into the person's daily live.

Furthermore, when body aches and pain symptoms occur, most people opt to use pain-relief patches or anti-inflammatory ointments because they are affordable and easily obtainable, while others will utilize massage therapy to ease the muscle tension and pain. However, while the effect of pain and inflammation relief can be achieved, the foregoing methods have disadvantages such as the market brands being too multifarious, and such medicine likely containing drugs and chemicals that can cause ill side effects. Moreover, if the pain-relief patch is used on the skin for long hours, symptoms such as redness, swelling and itching may appear on the affected area as a form of allergic reaction. Further, as some pain-relief patches contain non-steroidal anti-inflammatory drugs, repeated and long-term use may result in harmful side effects to the liver and kidneys.

In addition, ingredients in anti-inflammatory and/or analgesic ointments may also cause harm to the liver and kidneys. Furthermore, while these ointments are usually applied by simultaneously massaging an aching area, it is often difficult to accurately massage and relieve the aching area with one's own hands or even with an assistive device (e.g., massage rollers, sticks, or chairs). On the other hand, going to a clinic for professional massage therapy does yield certain benefits to people seeking pain relief, but it costs extra time and money that many people cannot afford. More importantly, certain illnesses such as fibromyalgia, chronic back pain with degenerative discs and degenerative joints disease, associated myofascial syndrome are chronic severe painful conditions that cannot be significantly relieved with mere pain-relief patches, anti-inflammatory and/or analgesic ointments, or massages alone. In these cases, people generally seek the aid of physical therapy.

As normal practice, a physical therapist will assess the symptoms and dysfunctions of a patient, and then intervene with device therapy, heat or ice therapy, hands-on therapy, and/or exercise therapy. In device therapy, since electrotherapy has pain-relieving, muscle-strengthening, muscle-atrophy delaying or preventing, muscle-spasm alleviating, and skin-blood-circulation improving characteristics, many people are using and accepting electrotherapy as a means for treating and relieving body pain and muscle tension related symptoms. Many methods of electrotherapy are currently available, such as low-frequency electrical stimulation (also referred to as transcutaneous electrical nerve stimulation, "TENS"), intermediate-frequency interference waves, etc., in which low-frequency electrical stimulation uses low-frequency waves with a frequency below 1,000 Hz (generally 0 to 100 Hz). In practical application, electrical nerve stimulation pulses generated by an electrotherapy device will stimulate the nerves through electrode pads adhered to the human skin to achieve the effect of relaxing tight muscles, improving local circulation, and providing pain-relief.

In addition, intermediate-frequency interference waves are intermediate-frequency waves ranging between 1,000 and 1,000,000 Hz. However, since heat is generated when the electric waves exceed 10,000 Hz, intermediate-frequency waves for clinical use typically range between 1,000 Hz to 10,000 Hz. In practical application, two sets of electrode pads are generally adopted for intermediate-frequency interference waves, with a frequency difference therebetween ranging from 0 to 100 Hz. For instance, 2,100 Hz and 2,000 Hz. The intermediate-frequency waves penetrate the skin such that current interference occurs in deep tissues to generate a low-frequency wave of 0 to 100 Hz. Therefore, through the aforementioned method of electrotherapy, appropriate electric currents can be utilized to achieve treatment purposes by stimulating the muscles.

Traditional electrotherapy devices suffer in terms of convenience since they are large in size and require electrode pads to be placed at specific locations. To combat these inconveniences, some manufacturers have developed electrotherapy devices for portable or household use (e.g., low-frequency therapeutic devices). Such electrotherapy devices are smaller in size, and are made to be more suitable for home use. In addition to receiving instructions from a doctor or therapist, these electrotherapy devices/systems have instructional manuals to enable patients to adhere electrode pads to painful positions and operate the device on their own, so as to conveniently achieve the effect of muscle relaxation, local circulation improvement and pain-relief. However, it has been discovered that when wishing to attach the electrode pads accurately and securely against the skin at the back of the shoulders or on the lower back or waist, a patient can often experience difficulties reaching behind his or her back, not being able to see behind himself or herself and to place the pads where the pads are needed on his/her own. In addition, the stickiness of the gel-coated electrode pads tends to become less adhesive with use. As such electrode pads become loose, poor conduction ensues, which causes the stimulation to become a very painful pin/needle-like sensation. Another major problem with these electrode pads is that if a user is moving about while working, walking, performing repetitive or large movements during exercise or playing sports, the surface of such an electrode pad can easily lose its full contact with the bare skin, similarly causing poor electrical conduction, which results in the stimulation becoming a very painful pin/needle-like sensation. Eventually, the treatment becomes ineffective, and the person experiences rather more pain instead of pain relief. Such electrode pads also tend to fall off if the user moves his or her body during the treatment, because these electrode pads are not provided with a mechanism to hold them securely in place. With the electrode pads tending to fall off rather easily, a treatment employing such electrode pads can often result in failure and disappointment. Without the help or presence of a nearby friend or family member, it is difficult for the user to reach behind his or her back since the user cannot see where he or she needs to place the electrode pads and reattach the electrode pads back onto the proper positions on the back of his or her upper shoulders, the lower back or waist.

Another common device therapy used by physical therapists and the general public is heat therapy. Commonly, a heating pad or electrode with heating elements is placed over the painful area. For the heat to transfer from the heating pad to the body, a person has to manually hold the heating pad firmly against the body, or a strap or a weighted object needs to be used to hold the heating pad firmly against the body in order for the heat to conduct to the tissue in pain. Also, the person needs to sit or lay down without much movement during the treatment. Otherwise, the heating pad or the electrode with heating elements will fall away from the body. If the heating pad sits loosely against the body, the heat transferred to the tissue will be insufficient, and the heat therapy treatment will not be effective. For heat therapy to be effective, the heating pads or electrode with heating elements must be held firmly against the body in order for the heat to transfer onto the body adequately for therapeutic effects. If the heating pad or the electrode with heating elements sits loosely over the body, the heat will have little to no effects on the body because the body tissue temperature will not rise significantly as needed to cause vasodilation and muscle relaxation. Therefore, a loose sitting heating pad does not increase blood circulation or cause muscle relaxation for the user.

These problems with traditional application and usage of the heating pad and electrode(s) with heating elements make it difficult for a person to apply heat therapy or electrotherapy to himself or herself. For the above-mentioned reasons, these traditional methods of applying a heating pad or electrode with heating elements are rather ineffective in pain relieving especially when the user is out moving about, working, walking, travelling, exercising or playing sports.

Therefore, the present disclosure aims to solve these aforementioned issues, to provide an electrotherapy and/or heat therapy related product that affords more effectiveness, and is easier to use and more practical to the user.

SUMMARY

In response to the above-referenced technical inadequacies associated with conventional electrotherapy and/or heat therapy related products and methods of application, the present disclosure manifests years of practical experience of the inventor in clinical practice treating chronic pain patients, designing, processing, and manufacturing and an unrelenting spirit in pursuit of innovation, which, combined with long hours of research and experimentation, has culminated in the conception and development of a garment having an adjustment mechanism for abutting at least one pad unit against a human body, with the aim of overcoming the above-referenced technical inadequacies and providing users with a more effective, practical and convenient heat therapy and/or electrotherapy treatment modality for relieving their body muscle tension and pain.

In one aspect, the present disclosure provides a garment structure having an adjustment mechanism for abutting at least one pad unit against a human body. The pad unit can be an electrode pad unit, a heating pad unit or an electrode pad unit formed cooperatively with a heating unit. The garment structure includes a garment body, at least one adjustment belt, at least one pad unit, and at least one removable electrotherapy/heat therapy device such as a TENS device. The garment structure can be provided with a removable battery pack in a specially designed harness. The harness is designed with electrical conductive connectors so the electrotherapy device and the battery pack can pass their energy to the electrode pad unit(s), the heating pad unit(s), and/or the electrode pad unit(s) formed cooperatively with at least one heating unit, so as to provide power for the electrode pad unit(s), the heating pad unit(s), and/or the electrode pad unit(s) formed cooperatively with at least one heating unit. The harness has a secure locking mechanism that works to hold the electrotherapy device and the battery pack securely and not allow the electrotherapy device or the battery to dislodge from the garment body even if the user is moving while working on the job or playing sport. Furthermore, the electrotherapy device and the battery pack can be easily removed from the garment body by unlocking the harness to prevent damage when the garment body need to be washed in water.

One unique character of this new garment structure is that the garment structure can be made into a shirt of any size and style. For example, it could be made into a dress shirt, golf shirt, tank top, T shirt, or any other style of shirt. The electrode pad unit(s), the heating pad unit(s), and/or the electrode pad unit(s) formed cooperatively with at least one heating unit can be made of at least metallic fabric materials to conduct heat and electrical pulses, while the rest of the garment structure, or a shirt made from the garment structure, can be made of any fabric materials that are commonly used in making garments. For example, it can be made of cotton, polyester, plastic, synthetic leather or any other materials. Another unique character of this garment structure, or a shirt made from the garment structure, is that the garment does not need to be a tight body fitting shaped shirt or made with highly elastic materials or compression materials. It is noted that while the garment structure, or a shirt made from the garment structure, can still be made into a typical body tight-fitting fitness compression shirt, it does not necessarily have to, thanks to the adjustable tightening mechanism of the garment structure. Specifically, specific areas of the garment structure can be pull towards the human body and held tightly against the body regardless if the garment structure fit snugly or loosely on the person.

The garment body is for covering a region of a human body and is wearable on at least the upper human body. The at least one adjustment belt has a first end connected to the garment body, and a second end having a fixing portion configured to be fixed to an outer surface of the garment body. The adjustment belt can drag an inner surface of the garment body to move in a direction toward a skin surface of the human body when the adjustment belt is pulled. The at least one electrode pad unit, the heating pad unit, or the electrode pad unit formed cooperatively with a heating unit is disposed on an inner side of the garment body. When the adjustment belt is pulled, the at least one electrode pad unit, heating pad unit, or electrode pad unit formed cooperatively with a heating unit is moved, along with a portion of the garment body that is dragged, to abut against the skin surface of the human body, so the at least one electrode pad unit, heating pad unit, or electrode pad unit formed cooperatively with a heating unit can pass the electrical stimulations and/or warmth directly, effectively and painlessly to the skin of the human body since the skin surface and the surface of the at least one electrode pad unit, heating pad unit, or electrode pad unit formed cooperatively with a heating unit are abutted tightly against each other, and held in that position without the at least one electrode pad unit, heating pad unit, or electrode pad unit formed cooperatively with a heating unit becoming loose or dislodged even with full body movement during the treatment, thus enabling good electrical conduction, heat conduction and effective treatment to be administered whether the person is resting or moving about at work, while playing sports or other activities. Since the electrode pad unit(s), the heating pad unit(s), and/or the electrode pad unit(s) formed cooperatively with at least one heating unit are secured against the body with the adjustable tightening mechanism, the user is free to move about without any worries that the electrode pad unit(s), the heating pad unit(s), and/or the electrode pad unit(s) formed cooperatively with at least one heating unit will become loose or fall off from the attached position on their body. The garment structure with the adjustable tightening mechanism for the electrode pad unit(s), the heating pad unit(s), and/or the electrode pad unit(s) formed cooperatively with at least one heating unit satisfies a user's need to easily self-administrate heat therapy and/or electrotherapy, as well as his or her need to have these therapies while he or she is resting or moving about at work, while sitting, walking, playing sports or travelling. The garment structure, or a shirt made thereof, with the at least one electrode pad unit, the heating pad unit, and/or the electrode pad unit formed cooperatively with a heating unit, and the adjustable tightening mechanism enable the user to self-administer heat therapy and/or electrotherapy anywhere, anytime with no restriction of activities or body movements during the therapy session. By using the garment structure, a user can relax his or her muscles, improve local circulation, and relieve pain while working, travelling exercising, playing sports or sleeping.

Another advantage of using this garment structure is that a user can stop the treatment anytime he or she wishes. The user can release the tightening mechanism, and then the electrode pad unit(s), the heating pad unit(s), and/or the electrode pad unit(s) formed cooperatively with at least one heating unit will not stay adhered to the skin surface. Instead, after the tightening mechanism is released, the garment structure returns to a loose state in which the user would feel more comfortable, and the garment structure would feel and functions like a regular garment.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

FIG. 15 is an exploded view of the assembly of the control device and the holder according to yet certain other embodiments of the present disclosure.

DETAILED DESCRIPTION

Figure 1:
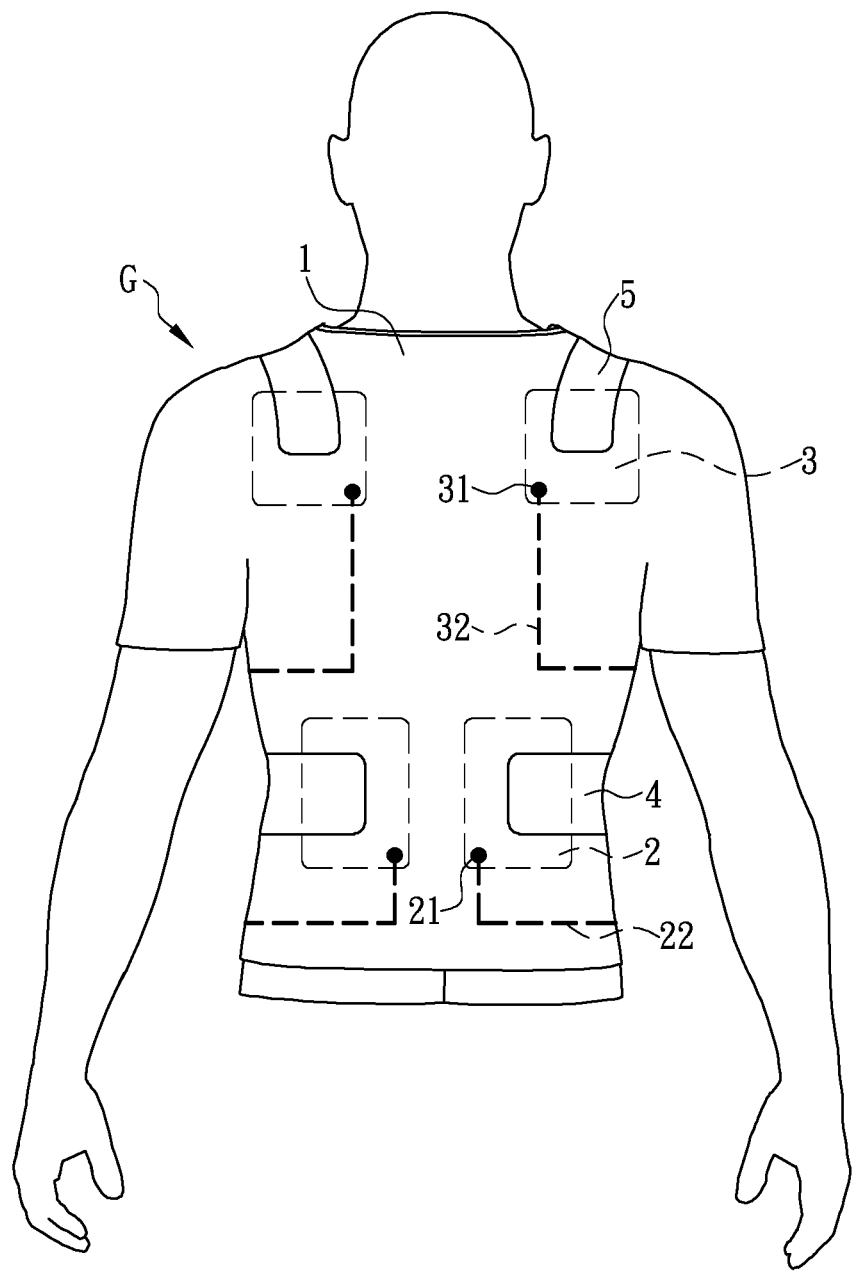
FIG. 1 is a schematic rear view of a garment structure according to the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, parts or the like, which are for distinguishing one component/part from another one only, and are not intended to, nor should be construed to impose any substantive limitations on the components, parts or the like, or be relevant to the sequence in which the components/parts are to be assembled or disposed in practical application.

In order to provide a user with a more convenient heat therapy and/or electrotherapy related product, a structure that combines at least one electrode unit and/or at least one heating unit to a garment (e.g., a top (defined as, for example, an item of clothing that is worn on the upper human body), a pair of pants, etc.) is disclosed to allow the user to conveniently undergo heat therapy and/or electrotherapy by wearing the garment. However, as different people have different physiques, for some users, electrode units cannot be firmly pressed against their skin when the garment is worn, causing a weaker stimulation of electric currents to the nerves and muscles, so that the therapeutic effect of electrotherapy is lost. Further, loose electrodes can cause painful stimulations due to poor electrical conduction, and a loose heating pad that is not firmly abutted against the body will not heat up the body tissue and provide very little to no benefits. Therefore, the present disclosure provides a garment structure G having an adjustment mechanism for abutting at least one electrode pad unit(s), heating pad unit(s), and/or electrode pad unit(s) formed cooperatively with at least one heating unit against a human body, so as to satisfy the user's need for easily and independently adjusting a pad unit at different positions, enabling each of the electrode pad unit(s), the heating pad unit(s), and/or the electrode pad unit(s) formed cooperatively with at least one heating unit to be firmly pressed against to a skin surface of the user, so as to allow the user to conveniently receive heat therapy and/or electrotherapy treatment in order to improve local circulation, relax tight muscles and relieve body pain resulting from everyday activity, serving one of the design purposes of the garment structure G that is providing heat therapy and/or electrotherapy to a person's body for the purpose of relaxing the muscles, improve local circulation and relieving the pain. Accordingly, the garment structure G allows the user to himself or herself administrate heat therapy and/or electrotherapy while resting or while moving around working, playing sports or doing other physical activities.

Referring to FIG. 1, in certain embodiments, the garment structure G includes a garment body 1, a plurality of first pad units 2, a plurality of second pad units 3, a plurality of first adjustment belts 4, and a plurality of second adjustment belts 5. However, in other embodiments, the garment body 1 can also be designed to include only one pad unit and one adjustment belt, while enabling the same adjustment mechanism described below. Further, while the garment body 1 is exemplified as a top that covers an area from the shoulder region to the waist region of the human body, the present disclosure is not limited in this aspect, as long as the garment body 1 can be worn on the human body and cover a certain region thereof. In certain embodiments, the garment structure G includes at least one pad unit fixated at the garment body 1. The pad unit is attached to a control device 6, so that the pad unit can pass the heat directly and efficiently to the body via conduction, and/or can pass the electrical stimulations directly, effectively and painlessly to the skin of the human body, since the skin surface and the surface(s) of the pad unit(s) are abutted tightly against each other, and held in that position without the pad unit(s) becoming loose or dislodged even with full body movement during treatment. Therefore, good electrical conduction and effective treatment can be administered whether the person is resting or moving about at work, while playing sports or other activities. The position(s) of the pad unit(s) on the garment body 1 may differ according to practical needs, and the present disclosure is not limited to any specific pad-unit position configuration or arrangement on the garment body 1. In certain embodiments, pad units can be positioned on both right and left sides of the lower back and of the upper shoulders area of the garment body 1. The adjustment belts 4 and 5 on the garment body 1 may work to pull and hold these pad units abutted against the body and skin of a user to provide direct heat therapy and/or electrotherapy.

Figure 3A:
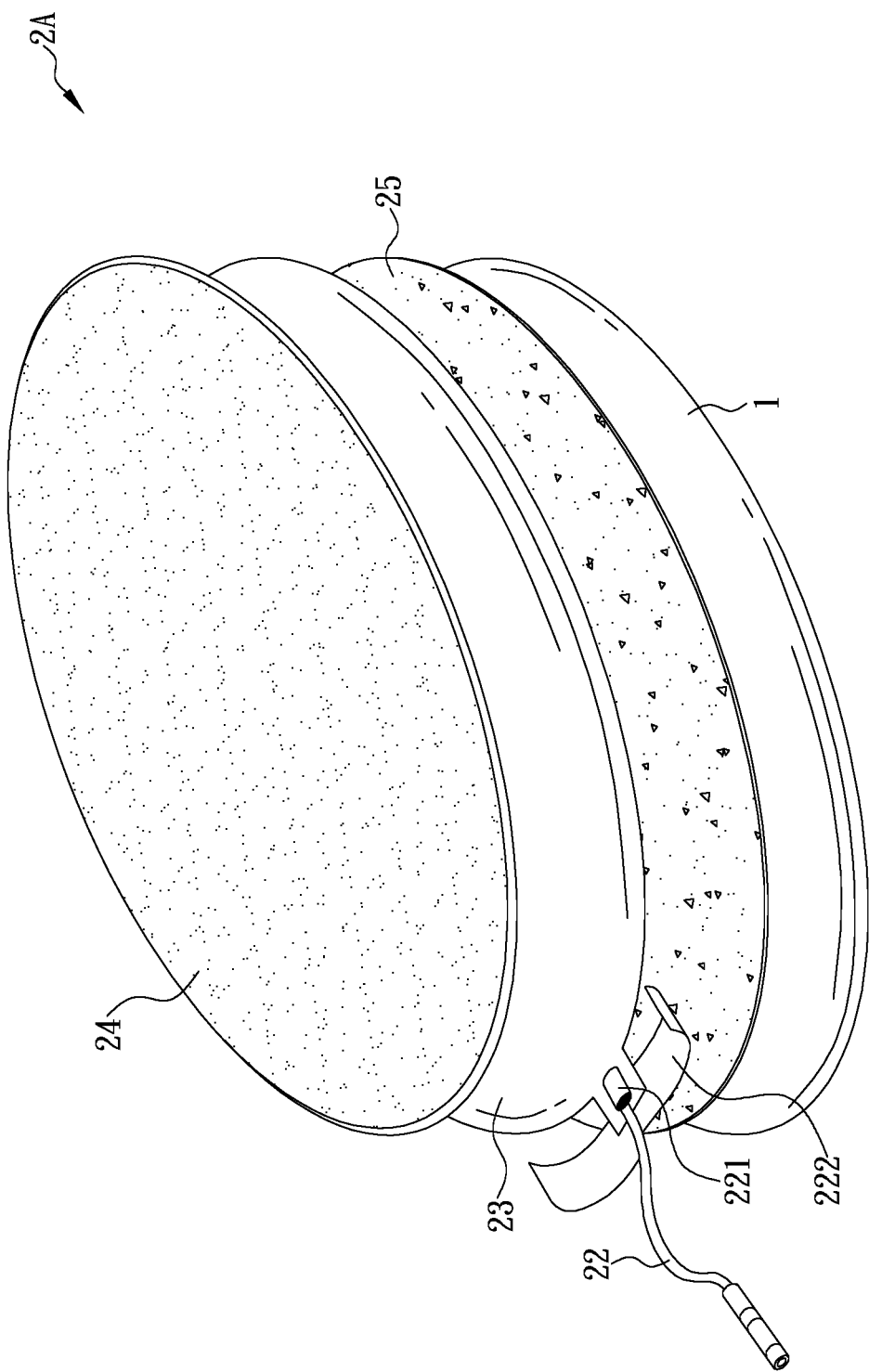
FIG. 3A is a schematic view of a pad unit being configured as an electrode pad unit according to the present disclosure.
Figure 3B:
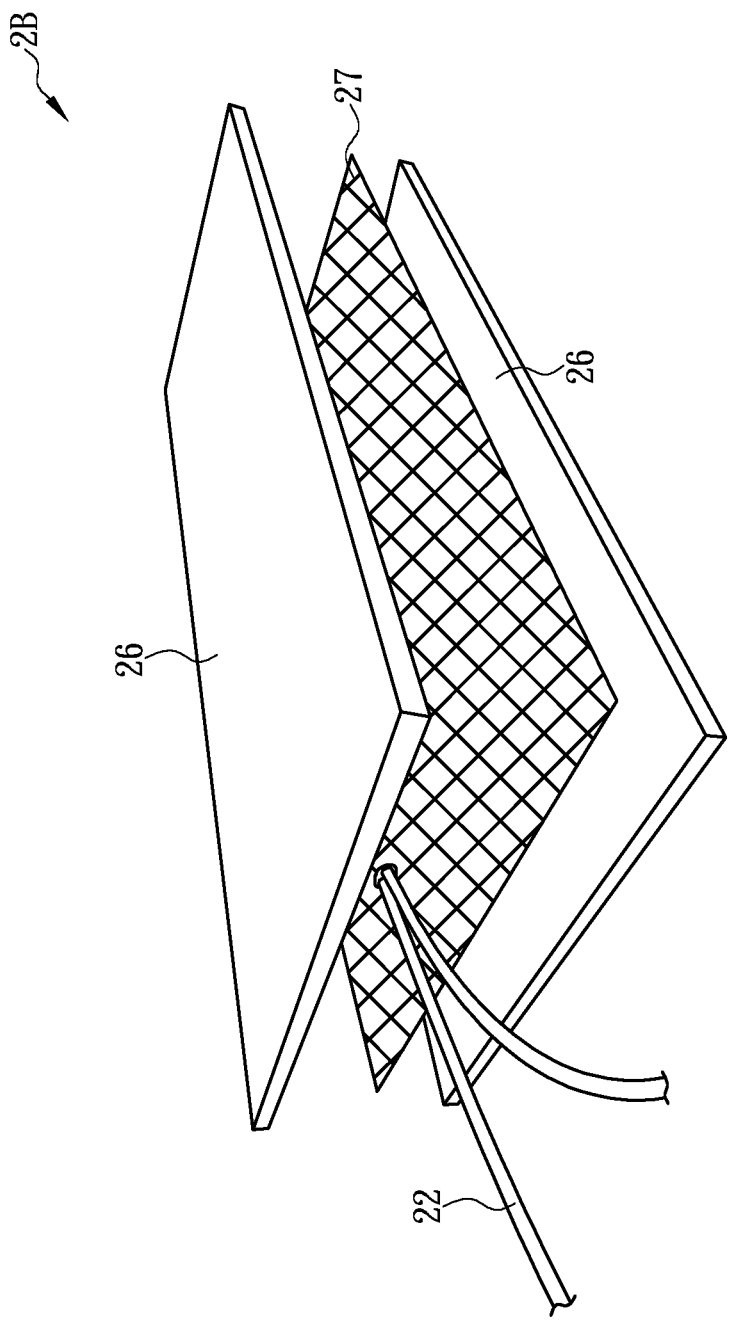
FIG. 3B is a schematic view of the pad unit being configured as a heating pad unit according to the present disclosure.

Referring to FIGS. 1 and 3A-3B, each of the pad units 2 and 3 can be configured as an electrode pad unit 2A, a heating pad unit 2B, or an electrode pad unit 2C that is formed cooperatively with at least one heating unit 28. In certain embodiments, the electrode pad unit 2A includes a conductive layer 23, a thin film layer 24 and an adhesion layer 25. The conductive layer 23 may be a layer of conductive fiber, conductive film, conductive cloth, aluminum foil, or a mixture thereof, or be made of other conductive materials. One side of the conductive layer 23 can be disposed with the thin film layer 24 (for example, a layer of conductive gel), while the other side of the conductive layer 23 can be disposed with the adhesion layer 25. Referring to FIG. 3A, a first conductive wire 22 can be electrically connected with the conductive layer 23, and can be fixated by a metal sheet 221 to an extension portion of the conductive layer 23. An insulative band 222 can be wound around and fix the metal sheet 221 and the first conductive wire 22. The adhesion layer 25 (for example, a layer of glue) can be fixed to an inner side of the garment body 1, so that for a user to use the electrode pad unit 2A, he or she only has to abut the thin film layer 24 against his or her skin to achieve the effect of electrotherapy. However, the electrode pad unit 2A is not limited to the structure as described supra. In certain embodiments, the thin film layer 24 may be omitted, and the conductive layer 23 is in direct contact with the skin. In certain embodiments, the adhesion layer 25 may be a conductive sheet (e.g., aluminum foil) coupled with a fabric (e.g., non-woven fabric, cotton fabric), so as to allow for better integration into the garment body 1.

In certain embodiments, referring to FIG. 3B, the pad unit 2 or 3 can be configured as a heating pad unit 2B that includes two cushion layers 26 (for example, layers made of non-woven fabric) and a heat-generating layer 27. The heat-generating layer 27 can be made of metal material (e.g., iron-chromium-aluminum alloy wires, nickel-chromium alloy wires, etc.), graphene, carbon fiber material, or other electrothermal materials, etc. In certain embodiments, the heat-generating layer 27 can be made of heating wire, a sheet of graphene, or a mixture thereof that heats up when electrical current is passed through the heat-generating layer 27. The heat-generating layer 27 can be sandwiched between the two cushion layers 26, and the outer surface of one of the cushion layers 26 (for example, the cushion layer 26 at the bottom of FIG. 3B) can be fixated on the inner surface of the garment body 1. At least one first conductive wire 22 can be electrically connected with the heat-generating layer 27, so that heat is generated by the heat-generating layer 27 and conducted away through the cushion layers 26. Therefore, when the heating pad unit 2B is in use, a user needs only to abut the other cushion layer 26 against the skin to achieve the effect of heat therapy. Warm compresses can allow blood vessels to relax so as to increase local blood circulation and increase the rate of metabolism, such that inflammatory substances are quickly expelled from the human body and self-healing abilities of the tissue can be improved. At the same time, warm compresses can increase soft tissue resilience and reduce muscle spasms, so as to relieve one's pain and relax one's emotions. In certain embodiments, the cushion layers 26 may be omitted, and the heat-generating layer 27 is in direct contact with the skin.

Further, warm compression and electrotherapy can work in tandem to provide a better therapeutic effect. In order to achieve the aforementioned effects, referring to FIGS. 1, 2 and 3C, the pad unit 2 or 3 can be configured as the electrode pad unit 2C formed cooperatively with at least one heating unit 28. The heating unit 28 can be disposed between the conductive layer 23 and the inner surface of the garment body 1. The heating unit 28 can be electrically connected to the first conductive wire 22 (not shown in FIG. 3C) so as to receive electric current from the control device 6, and transform the electric current from electric energy to thermal energy. In certain embodiments, the heating unit 23 can further be electrically connected to the control device 6 via another conductive wire other than the first conductive wire 22, so that the user can choose only one between electrotherapy and warm compression for use, and is not restricted to simultaneous usage of both.

Referring again to FIG. 3C, the electrode pad unit 2C formed cooperatively with at least one heating unit 28 includes one conductive layer 23, two cushion layers 26 (made of, for example, non-woven fabric), and one heat-generating layer 27 that is sandwiched between the two cushion layers 26. The two cushion layers 26 and the heat-generating layer 27 collectively form the heating unit 28. The outer surface of one of the two cushion layers 26 (such as the upper one of the two cushion layers 26 shown in FIG. 3C) can be disposed with the conductive layer 23, while the outer surface of the other one of the two cushion layers 26 (such as the lower one of the two cushion layers 26 shown in FIG. 3C) can be fixed at the corresponding inner surface of the garment body 1, such that the conductive layer 23 and the heating unit 28 can cooperatively form an integral structure and be conveniently combined with the garment body 1. In certain embodiments, the thin film layer 24 may be disposed on the side of the conductive layer 23 that is opposite to the side facing the cushion layer 26. Further, at least one first conductive wire 22 (not shown in FIG. 3C) can be electrically connected with the conductive layer 23 and the heat-generating layer 27, respectively. Therefore, when the electrode pad unit 2C is in use, a user needs only to abut the electrode pad unit 2C against his or her skin, and as the heat-generating layer 27 generates heat, the user can at the same time enjoy the benefits of warm compression while undergoing electrotherapy.

Figure 2:
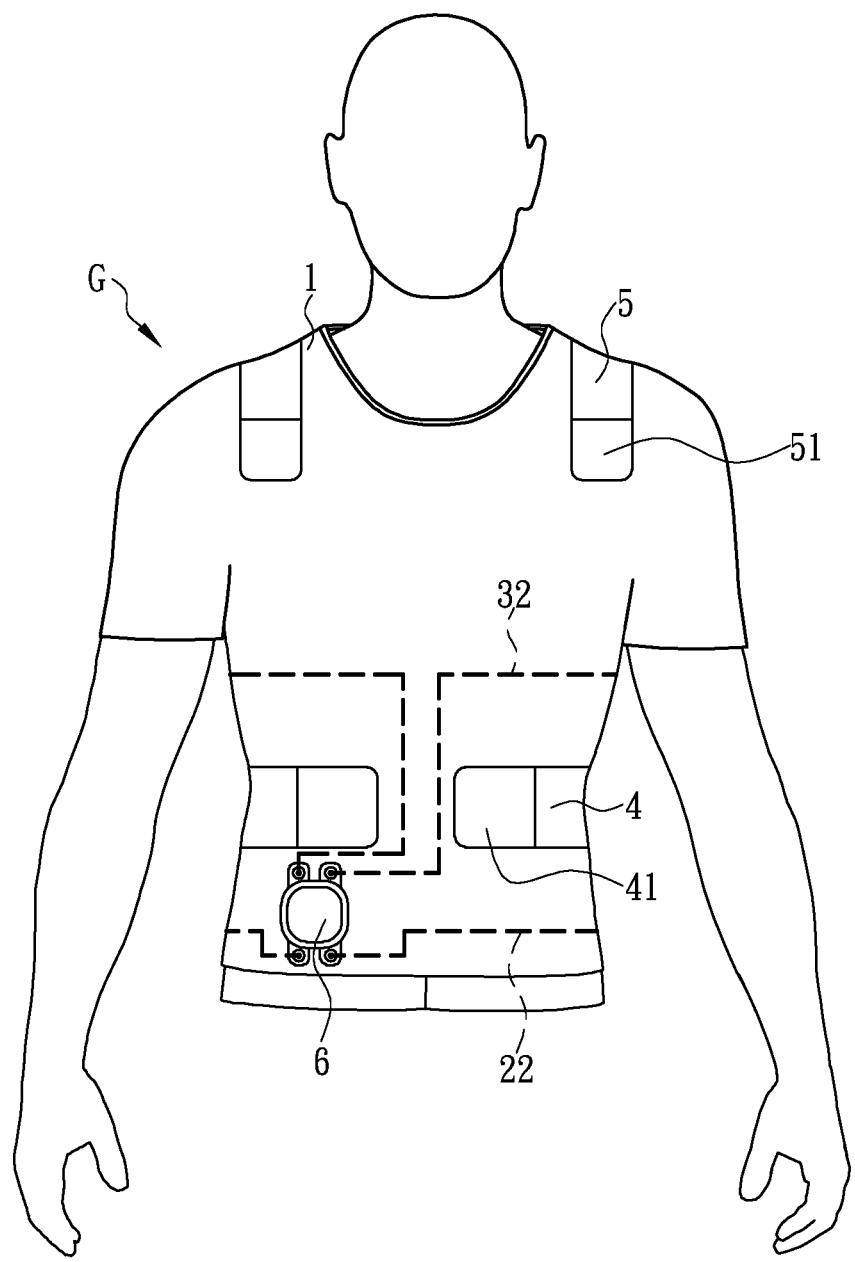
FIG. 2 is a schematic front view of the garment structure according to the present disclosure.
Figure 3C:
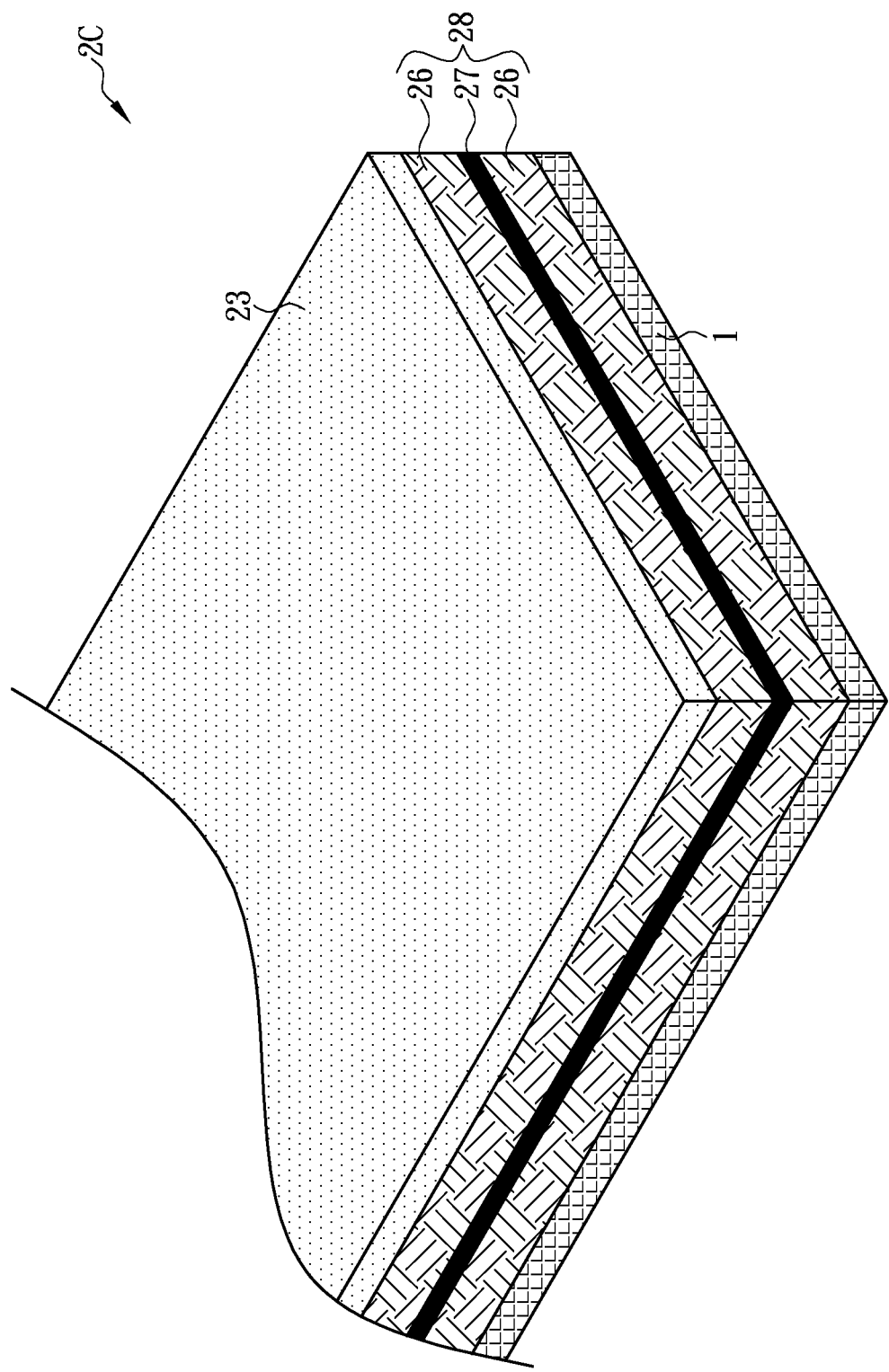
FIG. 3C is a schematic view of the pad unit being configured as an electrode pad unit formed with a heating unit according to the present disclosure.

Referring to FIGS. 1 and 2, the first adjustment belt 4 can be an elastic belt, or can have adjustment buckles, hooks, snap fasteners or buttons disposed thereon, etc., and any adjustment belt that is capable of adjusting its own length should be considered as the first adjustment belt 4 of the present disclosure. In certain embodiments, a first end of the first adjustment belt 4 can be connected (such as by being sewn) to an outer side of a back of the garment body 1, and correspond in position to the waist region of the human body. A second end of the first adjustment belt 4 can have a first fixing portion 41 (e.g., at least one hook-and-loop fastener, at least one button, etc.). When the second end of the first adjustment belt 4 is pulled and extends to a front of the garment body 1, the first fixing portion 41 can be fixed to an outer surface of the garment body 1. For instance, when the first fixing portion 41 is a hook-and-loop fastener, the outer surface of the garment body 1 can have a position-fixing portion that allows the hook-and-loop fastener to be fixed thereon. In certain embodiments, the outer surface of the garment body 1 can be made of a material that allows the hook-and-loop fastener to stick thereon.

Figure 4A:
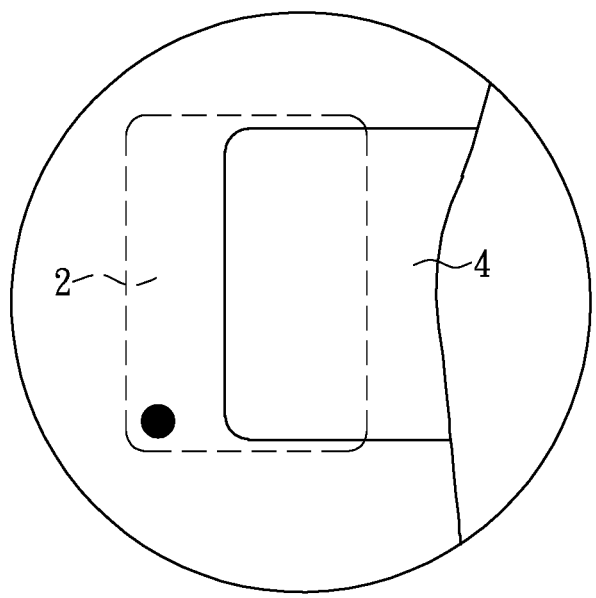
FIG. 4A is a schematic view showing a first adjustment belt being located within an area where a first pad unit is disposed according to the present disclosure.
Figure 4B:
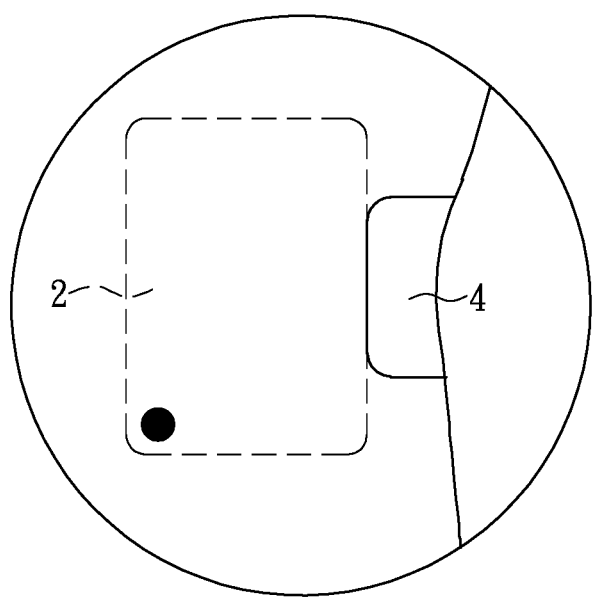
FIG. 4B is a schematic view showing the first adjustment belt being adjacent to the area where the first pad unit is disposed according to the present disclosure.

Further referring to FIGS. 1 and 2, in certain embodiments, at least one first pad unit 2 can be disposed on an inner side of the garment body 1, and corresponds to a position at the waist region of the human body. Moreover, when the first pad unit 2 is configured as the electrode pad unit 2A or 2C, the first pad unit 2 can contain poly(3,4-ethylenedioxythiophene) polystyrene sulfonate (i.e., PEDOT:PSS), or metallic fabric that is capable of conducting electricity, such as by covering a layer of PEDOT:PSS onto a plastic film to serve as the thin film layer 24, so as to improve the electrical conductivity of the first pad unit 2. Furthermore, the first end of the first adjustment belt 4 corresponds to the first pad unit 2. It should be noted that the word "correspond", as used to describe relationships between the first adjustment belt 4 and the first pad unit 2, encompasses the first end of the first adjustment belt 4 being located within an area where the first pad unit 2 is disposed (as shown in FIG. 4A), and being located adjacent to the area where the first pad unit 2 is disposed (as shown in FIG. 4B). In practical application, the first end of the first adjustment belt 4 is preferably located at a center of the first pad unit 2, or the width of the first end of the first adjustment belt 4 is preferably equal to or nearly equal to the width of the first pad unit 2.

Figure 5:
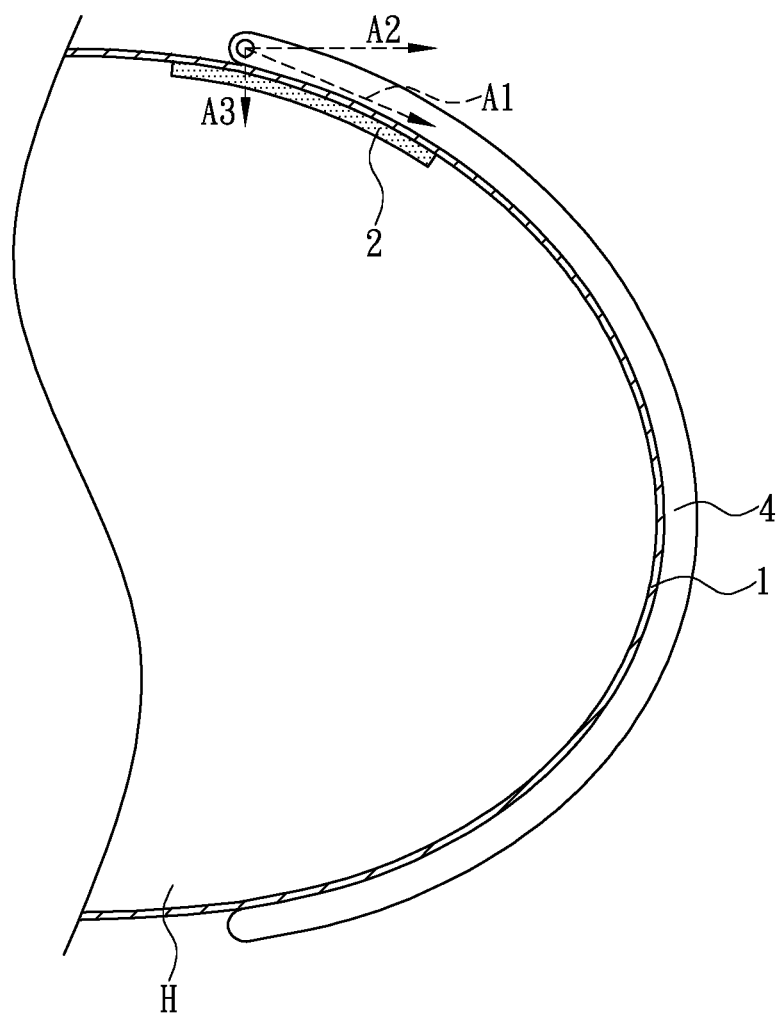
FIG. 5 is a schematic view showing the first adjustment belt being applied with a pulling force according to the present disclosure.

In continuance of the above, when the user puts on the garment body 1, the user can grasp and forcefully pull upon the second end of the first adjustment belt 4. During this process, referring to FIGS. 1, 2 and 5, the first end of the first adjustment belt 4 is therefore applied with a force A1 that comprises a horizontal component A2 and a vertical component A3. The vertical component A3 acts in a direction toward the human body H. Therefore, in certain embodiments, when the first adjustment belt 4 is pulled tight from the back to the front, the garment body 1 is synchronously dragged to move in a direction toward the corresponding waist region of the human body, such that the inner side of the garment body 1 is compelled to abut against the skin surface of the waist region. At this time, the first pad unit 2 moves along with the inner side of the garment body 1 to tightly abut against the waist region of the human body.

Further referring to FIGS. 1 and 2, in certain embodiments, the second pad unit 3 is also disposed on the inner side of the garment body 1, and corresponds in position to the shoulder region of the human body. The first end of the second adjustment belt 5 can be connected to the outer side of the back of the garment body 1, and corresponds to the second pad unit 3, while the second end of the second adjustment belt 5 has a second fixing portion 51. As mentioned above, when the second end of the second adjustment belt 5 is pulled and extends to the front of the garment body 1, and is fixed to the outer surface of the garment body 1, the first end of the second adjustment belt 5 is also applied with a vertical component in the direction toward the human body, so as to synchronously drag the garment body 1 to move in a direction toward the shoulder region of the human body, such that the second pad unit 3 moves along with the inner side of the garment body 1 to tightly abut against the shoulder region of the human body. Therefore, by virtue of the garment structure G of the present disclosure, when a user is alone, and each of the pad units 2, 3 are located at the back, the user can simply pull upon the adjustment belts 4, 5 to enable the corresponding pad units 2, 3 to easily and quickly abut tightly against the skin surface of the back, so as to avoid affecting the therapeutic effect of electrotherapy and/or heat therapy, and greatly improve the convenience of use.

Figure 6:
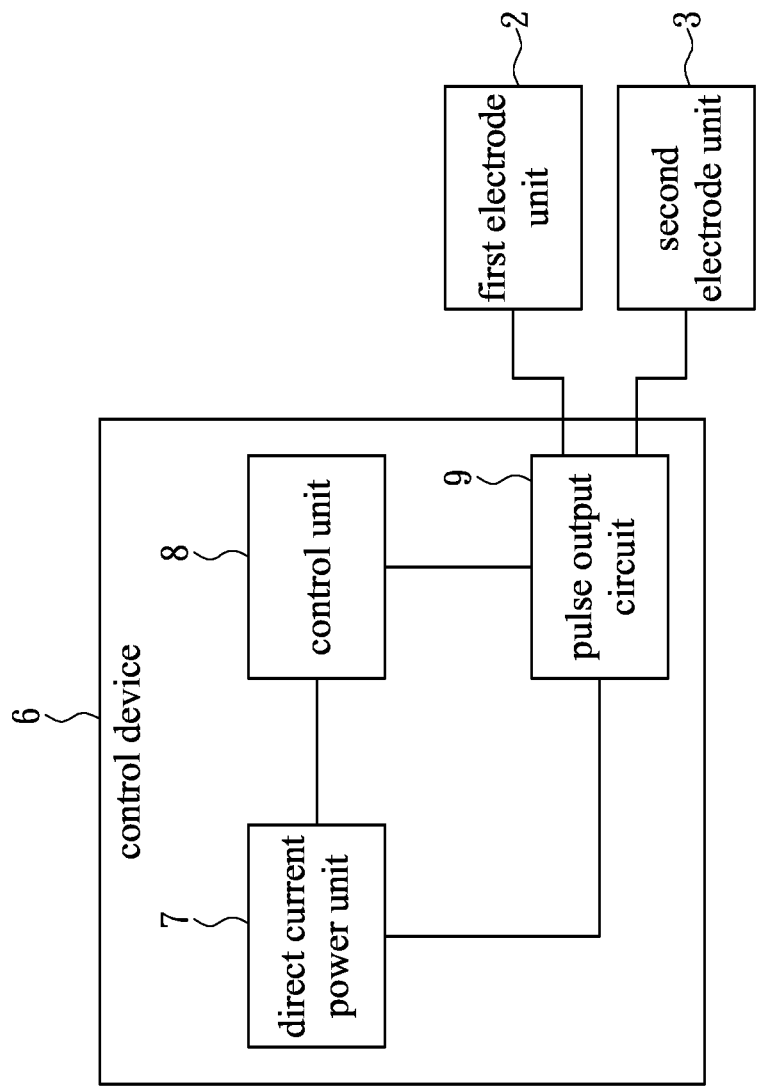
FIG. 6 is a hardware block diagram of a control device according to the present disclosure.
Figure 7:
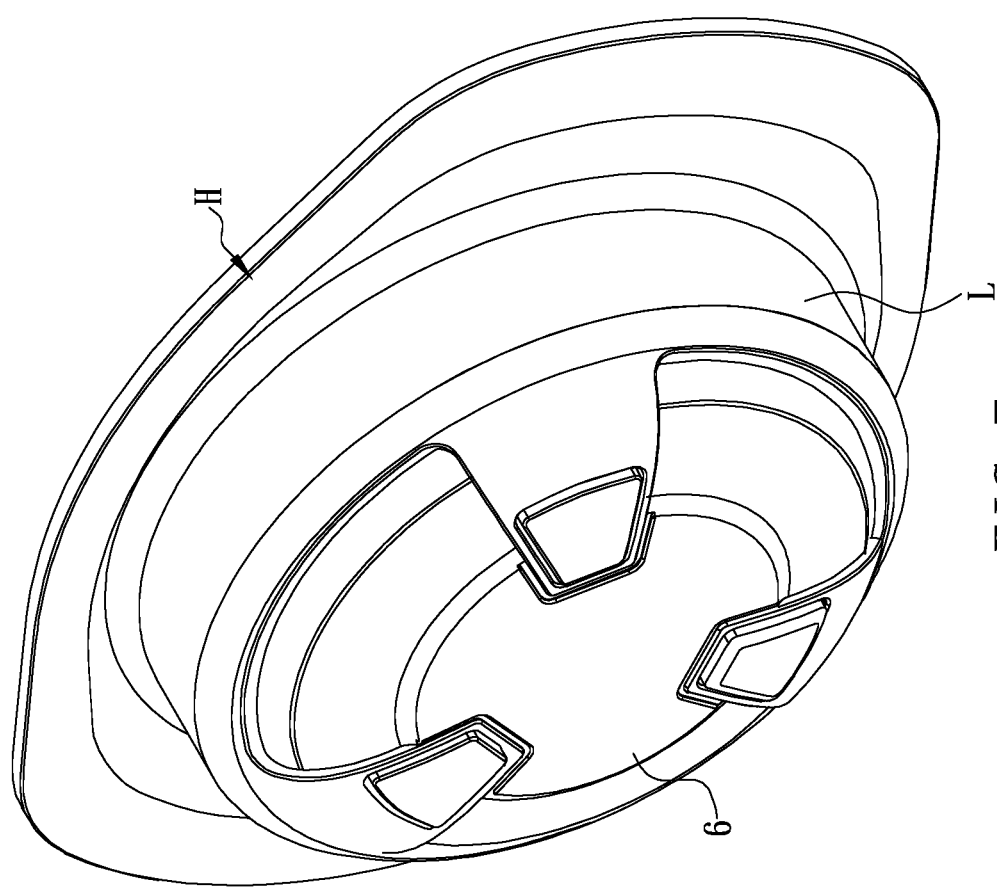
FIG. 7 is an assembled view showing a control device being harnessed in a holder by a secure releasable locking mechanism according to certain embodiments of the present disclosure.
Figure 8:
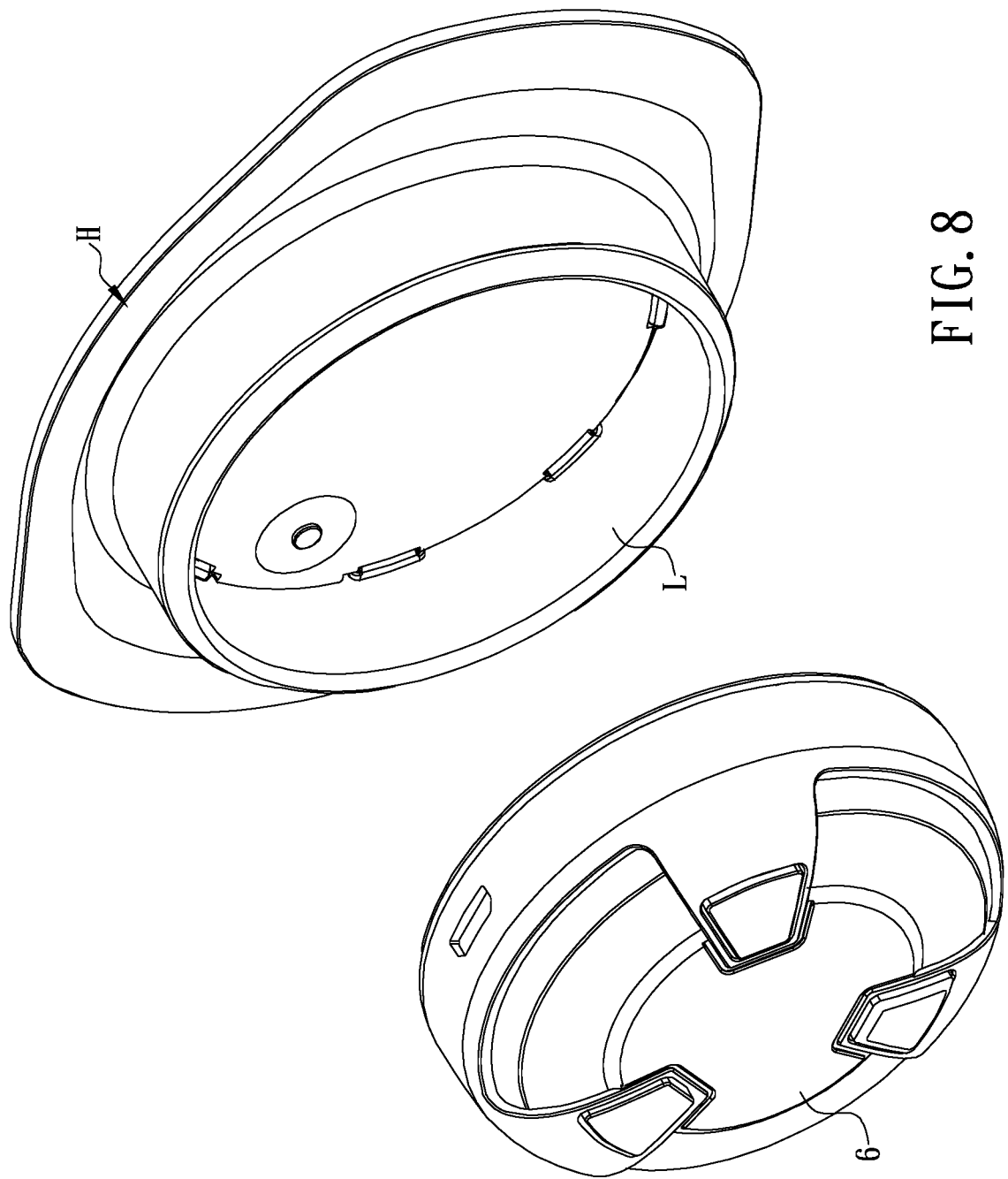
FIG. 8 is an exploded view of the assembly of the control device and the holder according to certain embodiments of the present disclosure.
Figure 9:
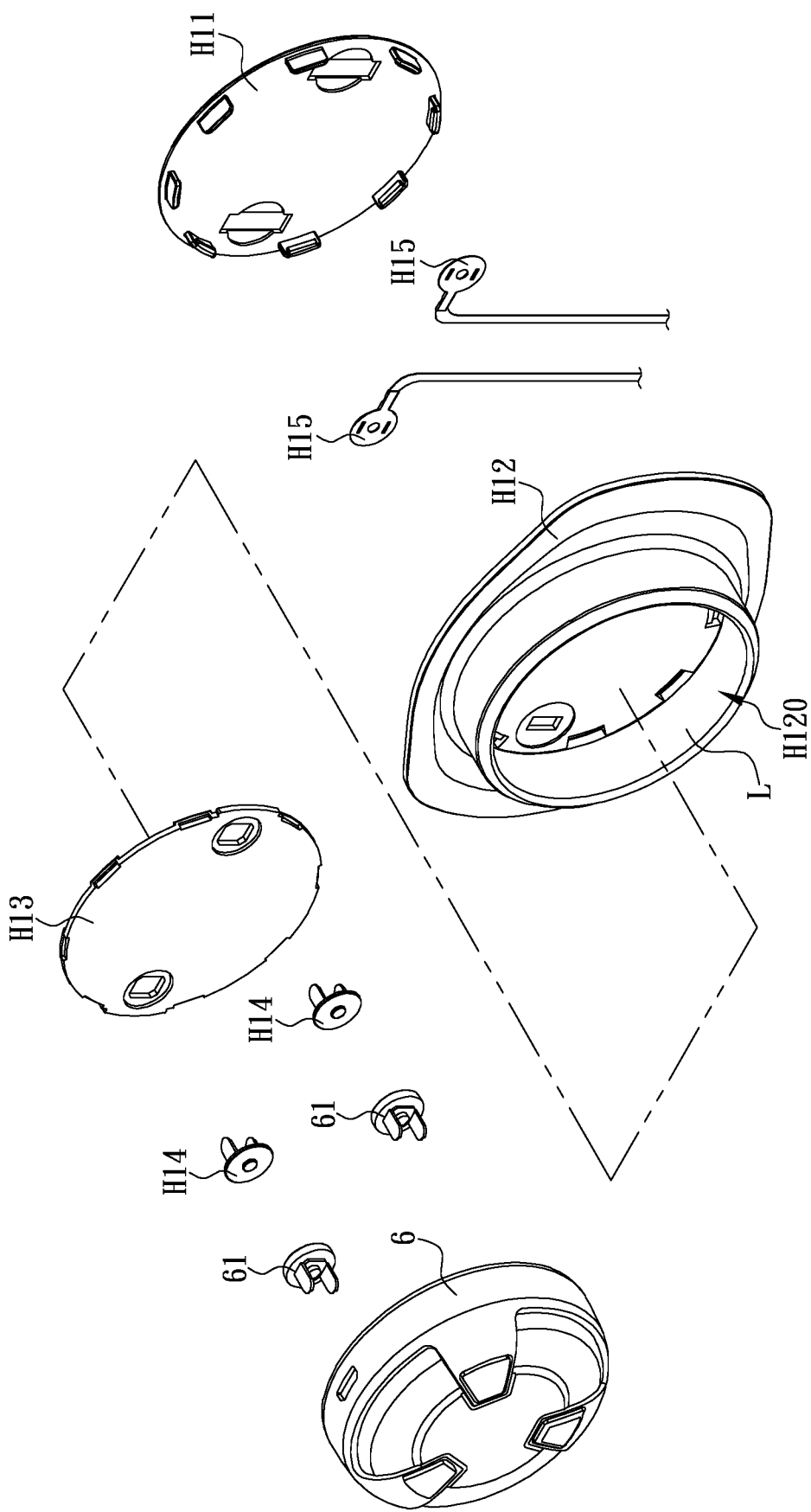
FIGS. 9 and 10 are exploded views showing the detailed components of the control device and the holder according to certain embodiments of the present disclosure.
Figure 10:
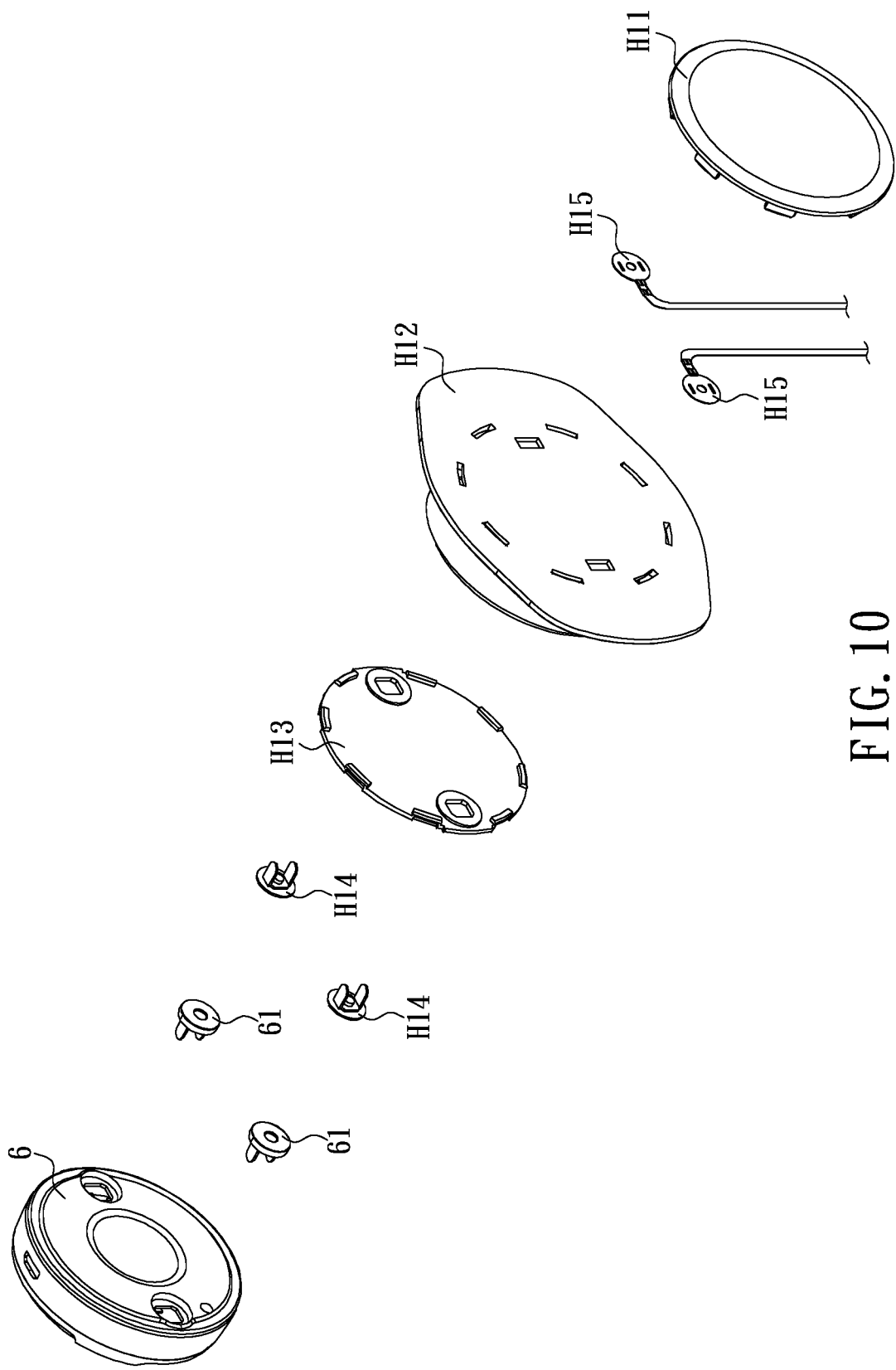

Furthermore, to enable the user to independently adjust a magnitude of electric current and/or warmth, a frequency, and a duration of the electrotherapy and/or heat therapy, the garment structure G further includes a control device 6. Referring to FIG. 6, the control device 6 at least includes a direct current power unit 7 (e.g., a dry cell), a control unit 8, and a pulse output circuit 9. The direct current power unit 7 can provide the control device 6 with power for operation, and the control unit 8 can transmit a plurality of control signals to the pulse output circuit 9, so that the pulse output circuit 9, after receiving power from the direct current power unit, can form at least one current pulse signal having a predetermined waveform based on the characteristics of each of the control signals, and transmit out the current pulse signal. Moreover, referring to FIGS. 1 and 2, the control device 6 can be electrically connected to the first pad unit 2 via the first conductive wire 22, and be electrically connected to the second pad unit 3 via a second conductive wire 32, so as to transmit the current pulse signal to each of the pad units 2, 3, and allow the first pad unit 2 and the second pad unit 3 to output electric current and stimulate the muscles of the user.

In certain embodiments, the control device 6 may be a portable electrotherapy/heat therapy device such as a TENS device or an electrical muscle stimulation (EMS) device, and may include a portable battery pack as the power source for electrotherapy therapy and/or heat therapy. The electrotherapy/heat therapy TENS device, and/or the battery pack, can be held on the garment body 1 by a holder H that is designed with a secure releasable locking mechanism L to enable the electrotherapy/heat therapy device and/or the portable battery pack to be released on demand from the garment body 1, for example, whenever the garment structure G needs to be washed in water, so as to prevent damage to the electrotherapy/heat therapy device or battery pack. Referring to FIGS. 7-15, the control device 6 can be harnessed in the holder H by the secure releasable locking mechanism L. In certain embodiments, the holder H with the releasable locking mechanism L may be a harness with a releasable lock. The holder H is provided with electrical conductive connectors so the portable electrotherapy/heat therapy device and/or the battery pack can pass their energy to the electrode pad unit(s) 2A, the heating pad unit(s) 2B, and/or the electrode pad unit(s) 2C formed cooperatively with at least one heating unit 28, so as to power the electrode pad unit(s) 2A, the heating pad unit(s) 2B, and/or the electrode pad unit(s) 2C formed cooperatively with at least one heating unit 28.

Referring to FIGS. 7-10, in certain embodiments, the holder H includes a base plate H11, a positioning body H12, an inner plate H13, a plurality of electrical conductive connectors H14, and a plurality of conductive-wire connectors H15. The base plate H11 and the positioning body H12 can be assembled with each other. A rear surface of the base plate H11 can be provided with at least one hook-and-loop fasteners, so as to be attached on the garment body 1. The positioning body H12 can be made of at least one elastic material, and formed with an accommodating slot H120 on the front surface thereof. The inner plate H13 can be arranged on the bottom surface of the accommodating slot H120. The inner diameter of the accommodating slot H120 can be slightly smaller than the outer diameter of the control device 6, for example, being smaller by 0.1% to 5% of the outer diameter of the control device 6, and the slot wall of the accommodating slot H120 can form the releasable locking mechanism L by, when the control device 6 is placed within the accommodating slot H120, expanding to a small extent, due to the flexibility of the accommodating slot H120, to wrap and abut firmly against the periphery of the control device 6, so as to position the control device 6 on the positioning body H12. When the positioned control device 6 is pulled outward from the positioning body H12 with a force that is greater than a force by friction that is exerted by the slot wall of the accommodating slot H120 (that is, the releasable locking mechanism L) to the control device 6, the control device 6 can be removed from the releasable locking mechanism L.

Referring again to FIGS. 7-10, the electrical conductive connectors H14 can be placed in the accommodating slot H120, and extend through, in sequence, the inner plate H13 and the bottom surface of the accommodating slot H120 and to the base plate H11. The conductive-wire connectors H15 can be located between the positioning body H12 and the base plate H11, and electrically connected to the corresponding electrical conductive connectors H14 respectively. Each of the conductive-wire connectors H15 can be electrically connected with at least one external conductive wire. Further, the rear side of the control device 6 can be provided with a plurality of electrical conductive members 61. After the control device 6 is placed in the accommodating slot H120, each of the electrical conductive members 61 can be electrically connected with a corresponding electrical conductive connectors H14, so that the electric current (current pulse signals) can pass in sequence through the electrical conductive member 61 and the electrical conductive connectors H14 and be transmitted to the conductive-wire connector H15. However, in certain embodiments, the electrical conductive connector H14 and the conductive-wire connector H15 may be integrated into one piece, and the electrical conductive connector H14 can be electrically connected with an external conductive wire.

Figure 11:
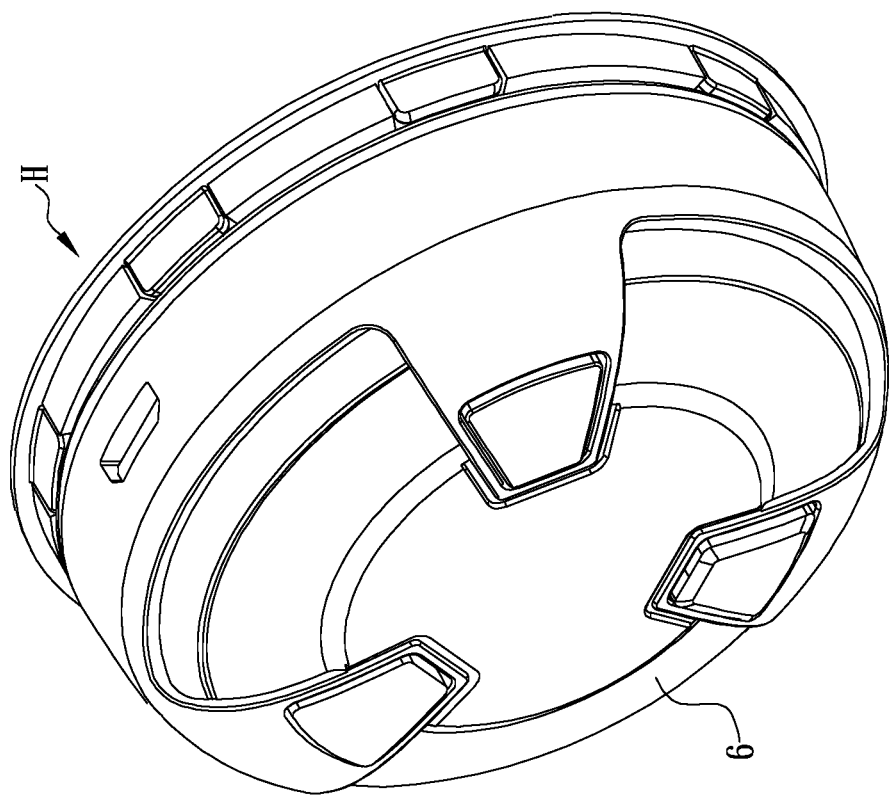
FIG. 11 is an assembled view showing the control device being harnessed in the holder according to certain other embodiments of the present disclosure.
Figure 12:
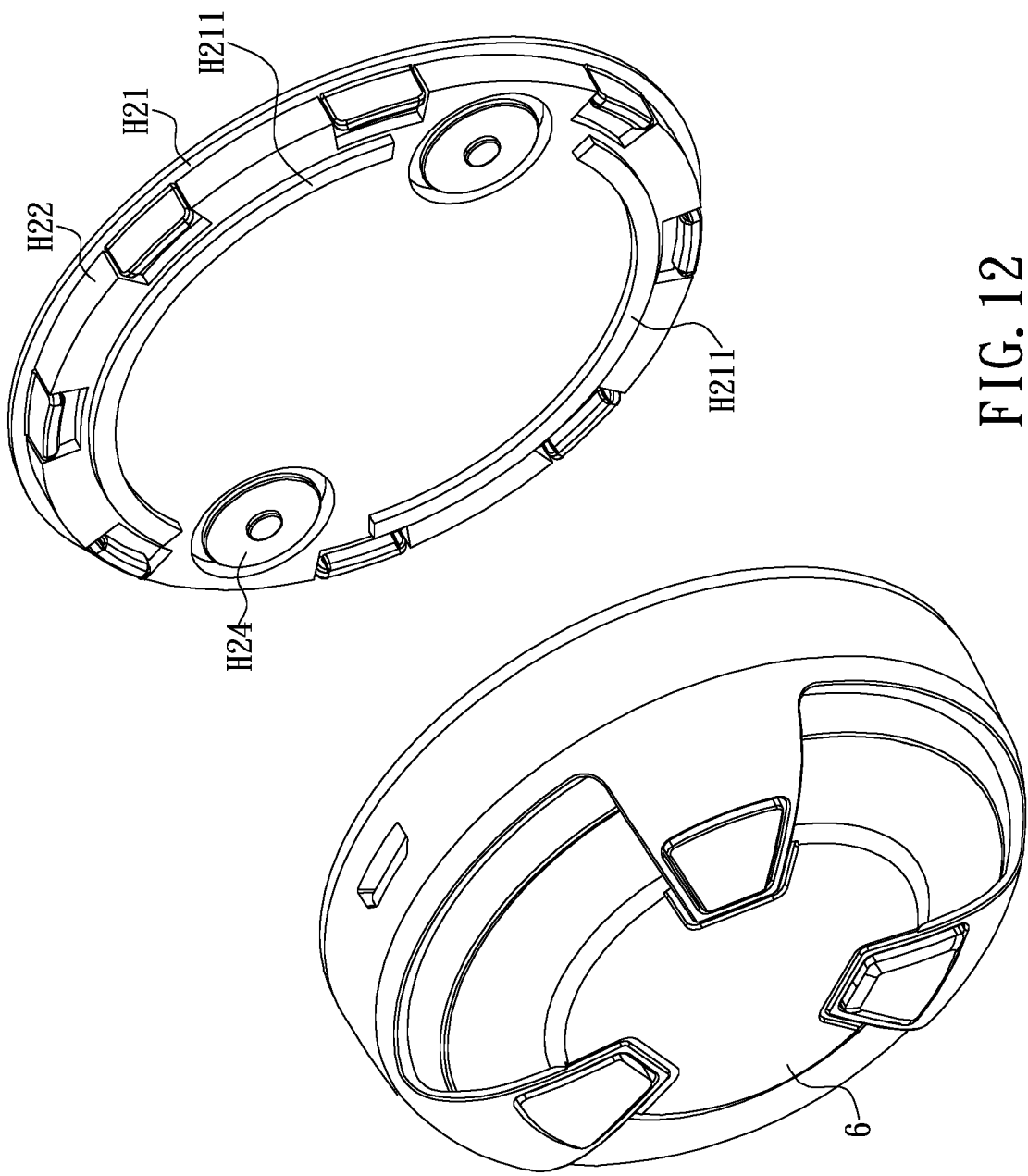
FIGS. 12 and 13 are exploded views of the assembly of the control device and the holder according to certain other embodiments of the present disclosure.
Figure 13:
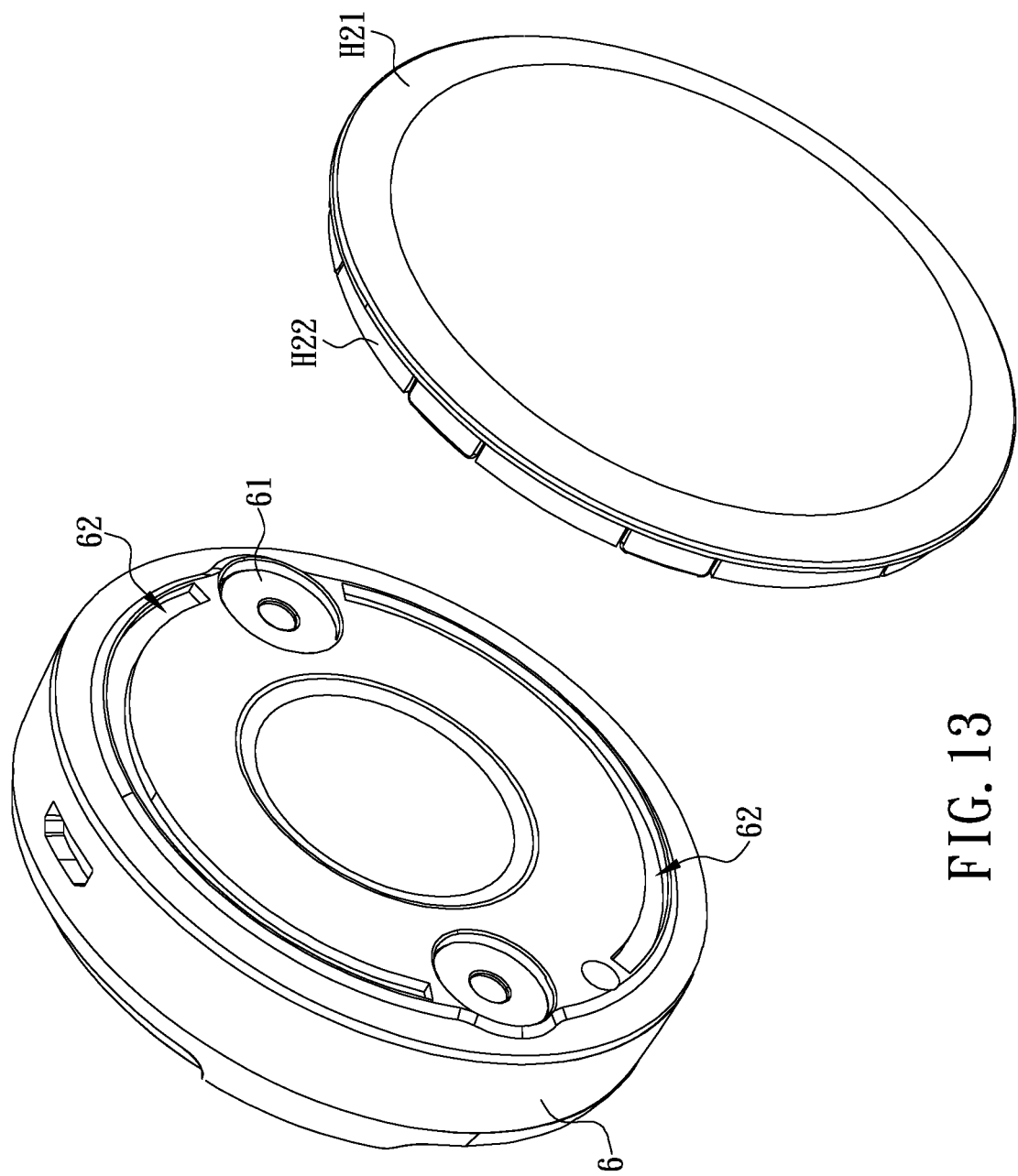

Referring to FIGS. 11-13, in certain embodiments, the holder H may include a base plate H21, a positioning body H22, and a plurality of electrical conductive connectors H24. The base plate H21 and the positioning body H22 can be assembled with each other, and the electrical conductive connectors H24 can be fixed on the positioning body H22. The front surface of the positioning body H22 can be protrudingly formed with at least one protruding rail H211 which serves as the releasable locking mechanism L. The rear surface of the control device 6 can be formed with at least one groove 62. The width and/or length of the groove 62 can be slightly smaller than the corresponding width and/or length of the protruding rail H211, for example, being smaller by 0.1% to 5% of the width of the protruding rail H211. When assembling the control device 6 to the positioning body H, the protruding rail H211 can be inserted into the corresponding groove 62, and the electrical conductive member(s) 61 can at the same time be electrically connected with the electrical conductive connectors H24. When the positioned control device 6 is pulled outward from the positioning body H22 with a force that is greater than the clamping force between the protruding rail(s) H211 and the corresponding groove(s) 62, the control device 6 can be removed from the releasable locking mechanism L.

Figure 14:
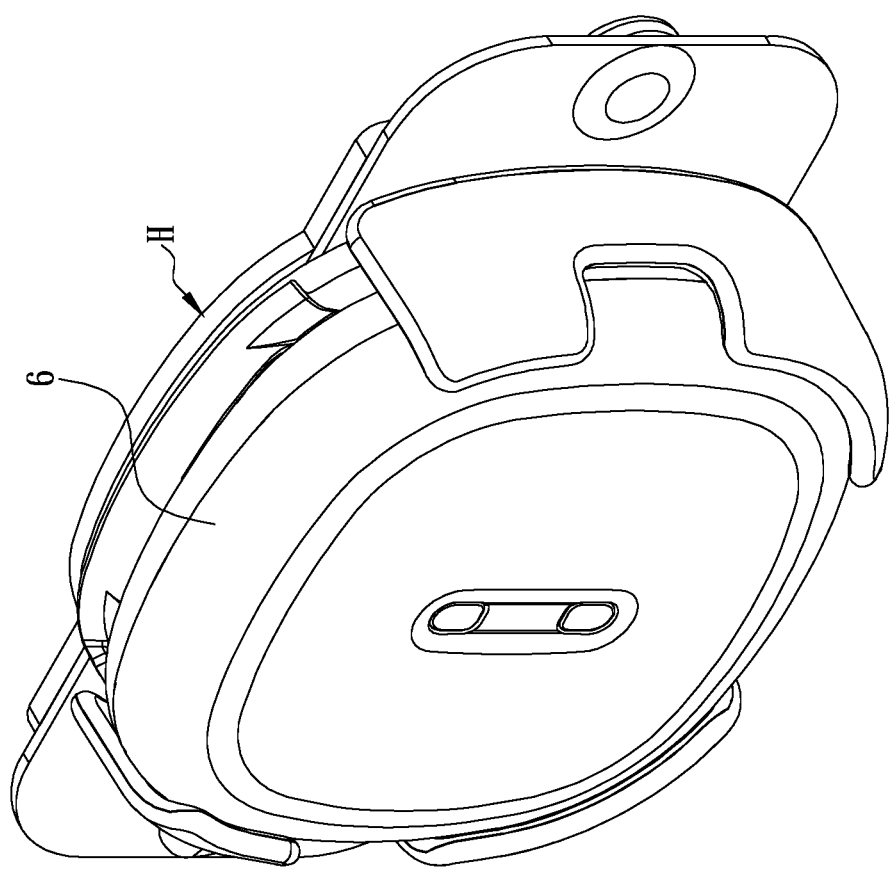
FIG. 14 is an assembled view showing the control device being harnessed in the holder according to yet certain other embodiments of the present disclosure.
Figure 16:
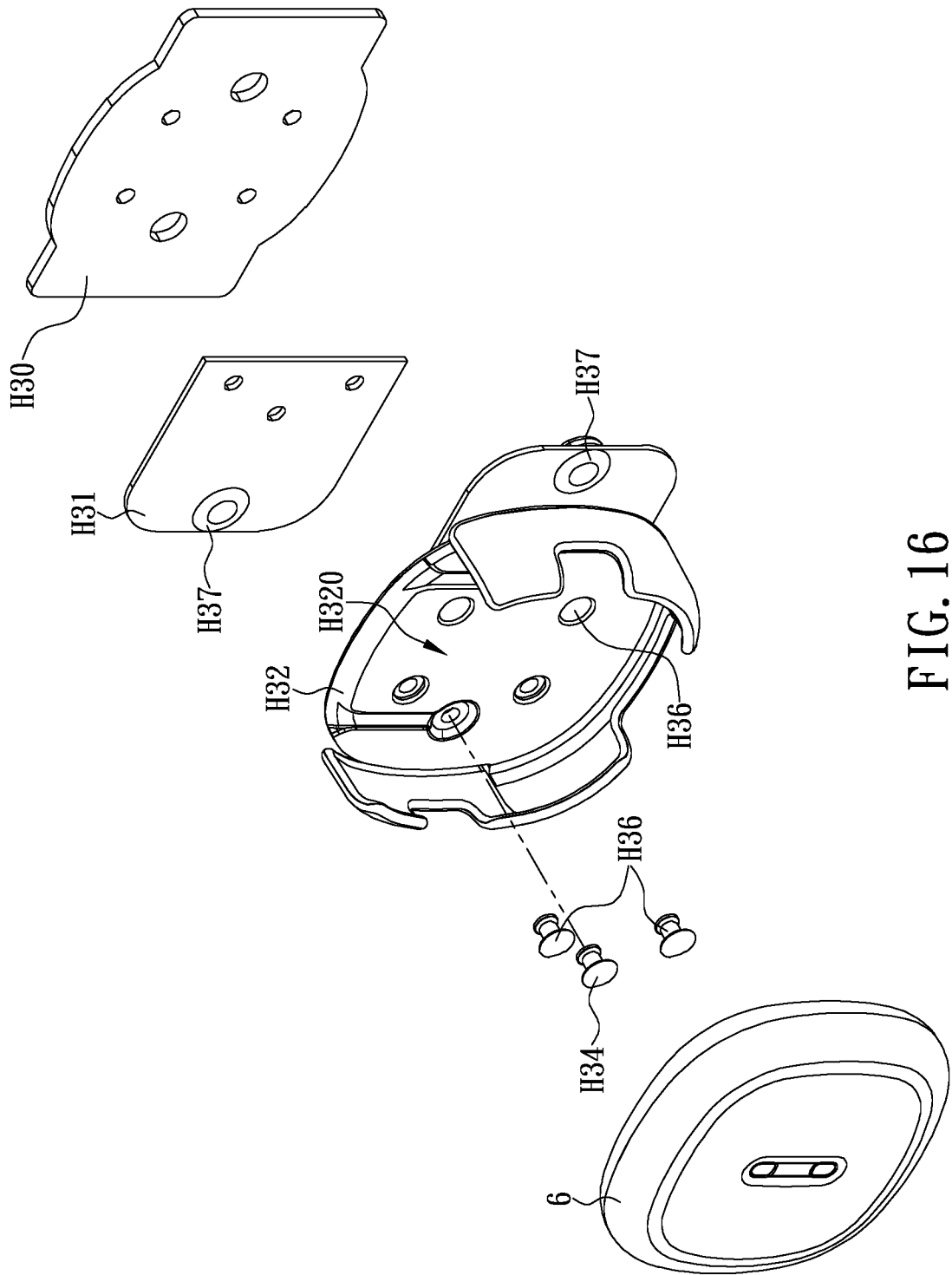
FIG. 16 is an exploded view showing the detailed components of the holder according to yet certain other embodiments of the present disclosure.

Referring to FIGS. 14-16, in certain embodiments, the holder H may include at least one base plate H31, a positioning body H32, and a plurality of electrical conductive connectors H34. The front side of the base plate H31 can abut against the rear side of the positioning body H32, and the rear side of the base plate H31 can abut against a connection plate H30 (for example, at least one hook-and-loop fastener). The base plate H31, the positioning body H32 and the connection plate H30 can be assembled into one piece through a plurality of fastening members H36. The front side of the positioning body H32 is formed with an accommodating room H320, and the control device 6 can be placed in the accommodating room H320, with the surrounding wall defining and of the accommodating slot H320 forming the releasable locking mechanism L. A part of the base plate H31 that is not blocked by the positioning body H32 when the positioning body H32 and the base plate H31 are assembled can be provided with at least one fixing member H37 (for example, a button). The fixing member H37 can be buckled with a corresponding fixing member on the garment body 1, so that the holder H can be more firmly positioned on the garment body.

Once the control device 6 is locked in place within the holder H, the user can move about and the control device 6 will not be displaced. The secure releasable locking mechanism L works to hold the electrotherapy/heat therapy device and/or the battery pack securely with the garment body 1, and to not allow the electrotherapy/heat therapy device and/or the battery to dislodge from the garment body 1 even if the user is moving while working on the job or playing sport.

When the garment structure G needs to be washed, the releasable locking mechanism L can be unlocked to release and remove the control device 6 before the garment structure G is washed in water, so as to prevent damage to the water sensitive electronics within the control device 6. The releasable locking mechanism L can be disposed on the garment body 1, and is connected to the at least one electrode pad unit(s) 2A, heating pad unit(s) 2B, and/or electrode pad unit(s) 2C formed cooperatively with at least one heating unit 28, in order for the electricity to flow from the control device 6 to the electrode pad unit(s) 2A, the heating pad unit(s) 2B, and/or the electrode pad unit(s) 2C formed cooperatively with at least one heating unit 28.

Referring again to FIGS. 1 and 2, in certain embodiments, a first metal buckle 21 is electrically connected to the first pad unit 2. One end of the first conductive wire 22 (that is, the external conductive wire described supra) can be fixed to the first metal buckle 21 (e.g., by winding, hooking, soldering, etc.), while the other end of the first conductive wire 22 is electrically connected to the conductive-wire connector H15 or the electrical conductive connectors H14, H24 or H34, so as to successfully transmit electric current (current pulse signals) from the control device 6 to the first pad unit 2. Similarly, one end of a second metal buckle 31 is electrically connected to the second pad unit 3, while the other end of the second metal buckle 31 is electrically connected to the conductive-wire connector H15 or the electrical conductive connectors H14, H24 or H34, so that the second conductive wire 32 can be fixed to the second metal buckle 31 and transmit electric current (current pulse signals) from the control device 6. In certain embodiments, for the purpose of portability, the control device 6 can have a miniaturized design to allow it to be placed at any position within the garment body 1. The control device can also be externally fastened on the outside of the garment body 1 or on other objects (e.g., a belt). For instance, a plurality of female buttons (that is, the corresponding fastening member described supra) can be disposed on the garment body 1, and a plurality of male buttons (for example, the fastening members H37 described supra) can be disposed on the control device 6 or the holder H, such that the control device 6 can be fixed onto the garment body 1 through the plurality of male and female buttons. Moreover, in practical application, the garment structure G can be used together with conventional large-sized electrotherapy devices, meaning that the user needs only put on the garment body 1, and have each of the first and second pad units 2, 3 be electrically connected to the control device 6 to receive electric current (current pulse signals) from the control device 6.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:
1. A garment structure, comprising:
   a garment body for covering a region of a human body and wearable on the human body;
   at least one adjustment belt having a first end connected to the garment body, and a second end having a fixing portion configured to be fixed to an outer surface of the garment body, and configured to drag an inner surface of the garment body to move in a direction toward a skin surface of the human body when the at least one adjustment belt is pulled; and
   at least one pad unit disposed on an inner side of the garment body, wherein the at least one pad unit is a first electrode pad unit, a heating pad unit or a second electrode pad unit cooperatively formed with at least one heating unit, and the at least one pad unit is configured to be moved, along with a portion of the garment body that is dragged, to abut against the skin surface of the human body when the at least one adjustment belt is pulled,
   wherein the first end of the at least one adjustment belt is a distal-most end of the at least one adjustment belt, and is connected to an area of an outer side of the garment body that is entirely within a boundary defined by a periphery of an area of the inner side of the garment body that has the same corresponding dimensions as, is aligned with an area of, and is disposed with, the at least one pad unit.

2. The garment structure according to claim 1, wherein the garment structure is configured to provide at least one of heat therapy and electrotherapy to a user whether the user is at rest or not or when the user is moving the user's body at work or while walking, exercising or playing sports.

3. The garment structure according to claim 1, wherein the garment body is configured to cover at least an area from a shoulder region of the human body to a waist region of the human body.

4. The garment structure according to claim 3, comprising a plurality of adjustment belts that include the at least one adjustment belt, each configured to drag the garment body to move in a direction toward at least one of the waist region and the shoulder region of the human body when pulled, and a plurality of pad units that include the at least one pad unit, each configured to be moved, along with the portion of the garment body that is dragged, to abut against at least one of the waist region and the shoulder region of the human body.

5. The garment structure according to claim 4, wherein the fixing portion is a hook-and-loop fastener.

6. The garment structure according to claim 1, wherein the at least one pad unit is the second electrode pad unit cooperatively formed with the at least one heating unit, and the heating unit is configured to form cooperatively with the corresponding second electrode pad unit into an integral structure, and located between a conductive layer of the second electrode pad unit and the inner surface of the garment body.

7. The garment structure according to claim 6, wherein the at least one heating unit includes two non-woven fabric layers and one heat-generating layer sandwiched between the two non-woven fabric layers, the conductive layer is located on a first outer surface of one of the two non-woven fabric layers, and a second outer surface of the other of the two non-woven fabric layers is fixed to a corresponding portion of the inner surface of the garment body.

8. The garment structure according to claim 1, wherein the at least one heating unit includes two non-woven fabric layers and one heat-generating layer sandwiched between the two non-woven fabric layers and is fixed to a corresponding portion of the inner surface of the garment body.

9. The garment structure according to claim 8, wherein the heat-generating layer is of a metal material, graphene, or carbon fiber material.

10. The garment structure according to claim 8, wherein the heat-generating layer is of a carbon fiber material.

11. The garment structure according to claim 1, further including a control device configured to transmit electric current to at least one of the first electrode pad unit, the heating pad unit and the second electrode pad unit, enable at least one of the first electrode pad unit and the second electrode pad unit to output electric current to stimulate a muscle, transmit electric current to at least one of the heating pad unit and the heating unit, and enable at least one of the heating pad unit and the heating unit to generate heat.

12. The garment structure according to claim 11, further including at least one metal buckle fixed to the garment body, electrically connected to at least one of the first electrode pad unit, the heating pad unit and the second electrode pad unit and the heating unit, and electrically connected to the control device via a conductive wire to receive electric current transmitted from the control device, and a locking mechanism configured to hold the control device in place, prevent the control device from dislodging from the garment body, and to be unlocked to release and remove the control device from the garment body to, when washing the garment structure in water, prevent damage to the control device.

13. The garment structure according to claim 12, wherein the control device includes:
a direct current power unit configured to supply to the control device power for operation of the control device;
a control unit configured to transmit a plurality of control signals; and
a pulse output circuit electrically connected to the control unit and configured to receive the control signals transmitted by the control unit, and form at least one current pulse signal having a predetermined waveform based on the control signals, and transmit the current pulse signal to the conductive wire.

14. The garment structure according to claim 1, wherein at least one of the first electrode pad unit and the second electrode pad unit contains poly(3,4-ethylenedioxythiophene) polystyrene sulfonate or metallic fabric capable of conducting electricity.

15. A garment structure, comprising:
a garment body for covering a region of a human body and wearable on the human body;
at least one adjustment belt having a first end connected to the garment body, and a second end having a fixing portion configured to be fixed to an outer surface of the garment body, and configured to drag an inner surface of the garment body to move in a direction toward a skin surface of the human body when the at least one adjustment belt is pulled; and
at least one pad unit disposed on an inner side of the garment body, wherein the at least one pad unit is a first electrode pad unit, a heating pad unit or a second electrode pad unit cooperatively formed with at least one heating unit, and the at least one pad unit is configured to be moved, along with a portion of the garment body that is dragged, to abut against the skin surface of the human body when the at least one adjustment belt is pulled,
wherein the first end of the at least one adjustment belt is a distal-most end of the at least one adjustment belt, and is connected to an area of an outer side of the garment body that crosses a boundary defined by a periphery of an area of the inner side of the garment body that has the same corresponding dimensions as, is aligned with an area of, and is disposed with, the at least one pad unit.

16. The garment structure according to claim 15, wherein the garment structure is configured to provide at least one of heat therapy and electrotherapy to a user whether the user is at rest or not or when the user is moving the user's body at work or while walking, exercising or playing sports.

17. The garment structure according to claim 15, wherein the garment body is configured to cover at least an area from a shoulder region of the human body to a waist region of the human body.

18. The garment structure according to claim 17, comprising a plurality of adjustment belts that include the at least one adjustment belt, each configured to drag the garment body to move in a direction toward at least one of the waist region and the shoulder region of the human body when pulled, and a plurality of pad units that include the at least one pad unit, each configured to be moved, along with the portion of the garment body that is dragged, to abut against at least one of the waist region and the shoulder region of the human body.

19. The garment structure according to claim 18, wherein the fixing portion is a hook-and-loop fastener.

20. The garment structure according to claim 15, wherein the at least one pad unit is the second electrode pad unit cooperatively formed with the at least one heating unit, and the heating unit is configured to form cooperatively with the corresponding second electrode pad unit into an integral structure, and located between a conductive layer of the second electrode pad unit and the inner surface of the garment body.

21. The garment structure according to claim 20, wherein the at least one heating unit includes two non-woven fabric layers and one heat-generating layer sandwiched between the two non-woven fabric layers, the conductive layer is located on a first outer surface of one of the two non-woven fabric layers, and a second outer surface of the other of the two non-woven fabric layers is fixed to a corresponding portion of the inner surface of the garment body.

22. The garment structure according to claim 9, wherein the at least one heating unit includes two non-woven fabric layers and one heat-generating layer sandwiched between the two non-woven fabric layers and is fixed to a corresponding portion of the inner surface of the garment body.

23. The garment structure according to claim 22, wherein the heat-generating layer is of a metal material, graphene, or carbon fiber material.

24. The garment structure according to claim 22, wherein the heat-generating layer is of a carbon fiber material.

25. The garment structure according to claim 15, further including a control device configured to transmit electric current to at least one of the first electrode pad unit, the heating pad unit and the second electrode pad unit, enable at least one of the first electrode pad unit and the second electrode pad unit to output electric current to stimulate a muscle, transmit electric current to at least one of the heating pad unit and the heating unit, and enable at least one of the heating pad unit and the heating unit to generate heat.

26. The garment structure according to claim 25, further including at least one metal buckle fixed to the garment body, electrically connected to at least one of the first electrode pad unit, the heating pad unit and the second electrode pad unit and the heating unit, and electrically connected to the control device via a conductive wire to receive electric current transmitted from the control device, and a locking mechanism configured to hold the control device in place, prevent the control device from dislodging from the garment body, and to be unlocked to release and remove the control device from the garment body to, when washing the garment structure in water, prevent damage to the control device.

27. The garment structure according to claim 26, wherein the control device includes:
- a direct current power unit configured to supply to the control device power for operation of the control device;
- a control unit configured to transmit a plurality of control signals; and
- a pulse output circuit electrically connected to the control unit and configured to receive the control signals transmitted by the control unit, and form at least one current pulse signal having a predetermined waveform based on the control signals, and transmit the current pulse signal to the conductive wire.

28. The garment structure according to claim 15, wherein at least one of the first electrode pad unit and the second electrode pad unit contains poly(3,4-ethylenedioxythiophene) polystyrene sulfonate or metallic fabric capable of conducting electricity.

* * * * *

UNITED STATES PATENT AND TRADEMARK OFFICE
CERTIFICATE OF CORRECTION

PATENT NO. : 11,849,778 B2
APPLICATION NO. : 16/926643
DATED : December 26, 2023
INVENTOR(S) : Hoi Ming Michael Ho It is certified that error appears in the above-identified patent and that said Letters Patent is hereby corrected as shown below:

In the Claims

Column 17, Line 22, Claim 22, Line 1: replace "claim 9" with --claim 15--

Signed and Sealed this
Twentieth Day of February, 2024

Katherine Kelly Vidal
*Director of the United States Patent and Trademark Office*